(12) United States Patent
Van Den Boom

(10) Patent No.: US 8,133,701 B2
(45) Date of Patent: Mar. 13, 2012

(54) DETECTION AND QUANTIFICATION OF BIOMOLECULES USING MASS SPECTROMETRY

(75) Inventor: Dirk Johannes Van Den Boom, La Jolla, CA (US)

(73) Assignee: Sequenom, Inc., San Diego, CA (US)

( * ) Notice: Subject to any disclaimer, the term of this patent is extended or adjusted under 35 U.S.C. 154(b) by 223 days.

(21) Appl. No.: 11/950,395

(22) Filed: Dec. 4, 2007

(65) Prior Publication Data
US 2008/0305479 A1 Dec. 11, 2008

Related U.S. Application Data

(60) Provisional application No. 60/868,718, filed on Dec. 5, 2006.

(51) Int. Cl.
- C12P 19/34 (2006.01)
- C12Q 1/68 (2006.01)
- C07H 21/02 (2006.01)
- C07H 19/04 (2006.01)

(52) U.S. Cl. ......... 435/91.1; 435/6; 536/23.1; 536/24.3; 536/26.6

(58) Field of Classification Search ............. 435/6, 91.1; 536/23.1, 24.3, 26.6
See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 5,174,962 A | 12/1992 | Brennan |
| 5,210,015 A | 5/1993 | Gelfand |
| 5,360,819 A | 11/1994 | Giese |
| 5,419,966 A | 5/1995 | Reed |
| 5,512,677 A | 4/1996 | Chern |
| 5,516,931 A | 5/1996 | Giese |
| 5,585,481 A | 12/1996 | Arnold |
| 5,665,539 A | 9/1997 | Sano |
| 5,696,251 A | 12/1997 | Arnold |
| 5,719,028 A | 2/1998 | Dahlberg |
| 5,736,626 A | 4/1998 | Mullah |
| 5,770,367 A * | 6/1998 | Southern et al. .......... 435/6 |
| 5,801,155 A | 9/1998 | Kutyavin |
| 5,942,610 A | 8/1999 | Nelson |
| 6,268,129 B1 | 7/2001 | Gut |
| 6,322,980 B1 | 11/2001 | Singh |
| 6,436,640 B1 | 8/2002 | Simmons et al. |

(Continued)

FOREIGN PATENT DOCUMENTS

WO  WO 2004/007755  1/2004

(Continued)

OTHER PUBLICATIONS

Burlingame et al. Anal Chem. 70:647R-716R (1998).
Ding and Cantor Proc Natl Acad Sci USA Mar. 18, 2003;100(6):3059-64.

(Continued)

Primary Examiner — Jezia Riley
(74) Attorney, Agent, or Firm — Grant Anderson LLP

(57) ABSTRACT

The present invention is directed in part to a method for detecting a target nucleic acid using detector oligonucleotides detectable by mass spectrometry. This method uses the 5' to 3' nuclease activity of a nucleic acid polymerase to cleave annealed oligonucleotide probes from hybridized duplexes and release labels for detection by mass spectrometry. This process is easily incorporated into a PCR amplification assay. The method also includes embodiments directed to quantitative analysis of target nucleic acids.

19 Claims, 14 Drawing Sheets

U.S. PATENT DOCUMENTS

| | | | |
|---|---|---|---|
| 6,511,809 B2 | 1/2003 | Baez |
| 6,514,700 B1 | 2/2003 | Singh |
| 6,613,509 B1 | 9/2003 | Chen |
| 6,635,452 B1 | 10/2003 | Monforte |
| 6,649,351 B2 | 11/2003 | Matray |
| 6,797,470 B2 | 9/2004 | Barany |
| 6,812,005 B2 | 11/2004 | Fan |
| 6,878,515 B1 | 4/2005 | Landegren |
| 6,890,741 B2 | 5/2005 | Fan |
| 7,902,345 B2 | 3/2011 | Van Den Boom |
| 2002/0006617 A1 | 1/2002 | Fan |
| 2002/0064779 A1 | 5/2002 | Landegren |
| 2003/0036064 A1 | 2/2003 | Stuelpnagel |
| 2003/0104434 A1 | 6/2003 | Fan |
| 2003/0108900 A1 | 6/2003 | Oliphant |
| 2003/0170684 A1 | 9/2003 | Fan |
| 2003/0194717 A1 | 10/2003 | Schmidt |
| 2003/0211489 A1 | 11/2003 | Shen |
| 2004/0121364 A1 | 6/2004 | Chee |
| 2004/0224352 A1 | 11/2004 | Fan |
| 2005/0053939 A1 | 3/2005 | Chenna et al. |
| 2005/0233351 A1 | 10/2005 | Landegren |
| 2005/0287533 A1 | 12/2005 | Ehrich |
| 2006/0024695 A1 | 2/2006 | Li |
| 2006/0040304 A1 | 2/2006 | Blumenfeld et al. |
| 2006/0160105 A1 | 7/2006 | Dhallan |
| 2006/0172319 A1 | 8/2006 | Yan |
| 2006/0234252 A1 | 10/2006 | Andersen |
| 2011/0160093 A1 | 6/2011 | Van Den Boom |

FOREIGN PATENT DOCUMENTS

| | | |
|---|---|---|
| WO | WO 2005/098042 | 10/2005 |
| WO | WO 2005/113804 | 12/2005 |
| WO | WO2006/056478 A1 | 6/2006 |
| WO | WO2006-056478 A1 | 6/2006 |
| WO | WO 2007/111937 | 10/2007 |
| WO | WO 2008/136868 | 11/2008 |

OTHER PUBLICATIONS

Haff, Nucleic Acids Res. (1997) 25:3749-3750.
Heid et al., Genome Methods 6:986-994, 1996.
Jurinke et al., Adv Biochem Eng Biotechnol (2002) 77:57-74.
Kaiser et al., J. Biol. Chem. 274:21387-21394 (1999).
Lyamichev et al., Proc. Natl. Acad. Sci. USA 96:6143-6148 (1999).
Ma et al., J. Biol. Chem. 275:24693-24700 (2000).
Reddy et al., Pharmacol. Therap. 84:1-111(1999).
Brent et al., Nat Methods. Jan. 2005;2(1):31-7.
Ross, Anal. Chem (1997) 69:4197.
Verbeck at al., In the Journal of Biomolecular Techniques vol. 13, Issue 2, 56-61.
Walker, et al., Biopolymers 44:323-334 (1997.
Wemmer & Dervan, Current Opinon in Structural Biology 7:355-361 (1997).
White, Trends in Biotechnology (1996) 14(12); 478-483.
Zimmer & Wahnert, Prog. Biophys. Molec. Bio. 47:31-112 (1986).
Zhang et al., "Location of abasic sites in Oligodeoxynucleotides by tandem mass spectrometry and by a chemical initiated by an unusual reaction of the ODN with MALDI matrix", Journal of the American Society for Mass Spectrometry, vol. 13, 2002, pp. 1418-1426.
International Search Report and Written Opinion for PCT/US2008/065822 mailed Dec. 19, 2008.
International Search Report and Written Opinion for PCT/US2007/86425 mailed:Dec. 22, 2008.
U.S. Appl. No. 12/133,327, filed Jun. 4, 2008, Van den Boom.
Verbeck et al., in the Journal of Biomolecular Techniques vol. 13, Issue 2, 56-61, 2002.
Isola et al., "Matrix-assisted laser desorption/ionization detection of polymerase chain reaction products by utilizing the 5'-3' exonuclease activity of *Thermus aquaticus* DNA polymerase," Rapid Communications in Mass Spectrometry, vol. 17, No. 6, 2003, pp. 532-537.
Extended European Search Report dated Sep. 21, 2010 in European Application No. EP 07874342 filed on Dec. 4, 2007.

\* cited by examiner

PCR F1-4 : TARGET NUCLEIC ACID SPECIFIC PCR FORWARD PRIMER
F1 ⟶ REGION 1 AND SO ON

PCR R1-4 : TARGET NUCLEIC ACID SPECIFIC PCR REVERSE PRIMER
R1 ⟶ REGION 1 AND SO ON

L1 : DETECTOR OLIGONUCLEOTIDE FOR TARGET REGION 1 WITH
5' NON-COMPLEMENTARY SEQUENCE OF LENGTH L1

L2 : AS ABOVE FOR REGION 2
5' NON-COMPLEMENTARY SEQUENCE OF LENGTH L2

L3, L4 : AS ABOVE

SEQUENCE LISTING

```
<160> NUMBER OF SEQ ID NOS: 37

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Pro Lys Pro Gln Gln Phe Phe Gly Leu Met
1               5                   10

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cctctcactg ttgcctgcat t                                           21

<210> SEQ ID NO 3
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 3
agtgcctgcg cgaacatt                                                       18

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aaaaaaattg ctgtctgatc tttatcctcc gttccct                                  37

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgccctcttc ttgtggatg                                                      19

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaacacggca ttcttccttt c                                                   21

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aaaaaaaatc tggccaagtt tcaactctgc tcgct                                    35

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acgttggatg atattctaga ctcttccaag cc                                       32

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 9
acgttggatg aaaaagagga gtgtcactct ac                32

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(15)
<223> OTHER INFORMATION: Locked nucleic acid

<400> SEQUENCE: 10
aaaaaaaaaa aaatttgcaa agcccagcac tga                33

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acgttggatg atgttagcca ggattgtctc g                31

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acgttggatg acacctgtaa tcccagcatt tt                32

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(11)
<223> OTHER INFORMATION: Locked nucleic acid

<400> SEQUENCE: 13
aaaaaaaaag ctgaggtgct tggatcacga                30

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acgttggatg caatcccgtg tctttcct                28

```
<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acgttggatg gaaccaaata ctgtgtattc cc                                    32

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(10)
<223> OTHER INFORMATION: Locked nucleic acid

<400> SEQUENCE: 16
aaaaaaaaat ggcttcccag gagtttgagg                                       30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acgttggatg tttacatcaa caaacaaggg                                       30

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acgttggatg ctactgggtc tagccttata at                                    32

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(13)
<223> OTHER INFORMATION: Locked nucleic acid

<400> SEQUENCE: 19
aaaaggaaaa aagaggttga catgaagtca tttgct                                36

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 20
acgttggatg tcactgggat caggacagac                                         30

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acgttggatg agaggaaact gcttcccaaa c                                       31

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(16)
<223> OTHER INFORMATION: Locked nucleic acid

<400> SEQUENCE: 22
aaaaaaaaaa aaaaaagctg ccagcaagga gcct                                    34

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
acgttggatg gatgggtttt ctatgtgtgg g                                       31

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
acgttggatg tgagtctctt aatagcactg ag                                      32

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(12)
<223> OTHER INFORMATION: Locked nucleic acid

<400> SEQUENCE: 25
aaaaaaaaaa acgggaggag tcagtgggga                                         30

<210> SEQ ID NO 26

```
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acgttggatg agctaattac tcatttcccc ag                                    32

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
acgttggatg agactcaaca ggacaagaga c                                     31

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(17)
<223> OTHER INFORMATION: Locked nucleic acid

<400> SEQUENCE: 28
aaaaaaaaaa aaaatgagg acttgttttg attgaaccaa                             40

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
acgttggatg tgcagaaaag accaaaggaa tc                                    32

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
acgttggatg atagatgcca cataacttga gc                                    32

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(13)
<223> OTHER INFORMATION: Locked nucleic acid
```

```
<400> SEQUENCE: 31
aaaaaaaaaa aacgaggatc agggagcacc c                                    31

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
acgttggatg aacgttttac cgaagtgttg t                                    31

<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
acgttggatg aagccaaagg ctaatatgta gg                                   32

<210> SEQ ID NO 34
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(14)
<223> OTHER INFORMATION: Locked nucleic acid

<400> SEQUENCE: 34
aaaaaaaaaa aatgatgaac tacacggcaa ttattga                              37

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
acgttggatg aggcaaaatg tactatgcct ac                                   32

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
acgttggatg tcctgtagtc tcaactattc ag                                   32

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence: Synthetic
```

```
                    oligonucleotide
<220> FEATURE:
<221> NAME/KEY: modified_base
<222> LOCATION: (11)..(12)
<223> OTHER INFORMATION: Locked nucleic acid

<400> SEQUENCE: 37
aaaggaaaaa atgctcactt gggcgaagga g                                       31
```

DETECTION AND QUANTIFICATION OF BIOMOLECULES USING MASS SPECTROMETRY

RELATED PATENT APPLICATION

This patent application claims the benefit of U.S. provisional patent application No. 60/868,718, filed Dec. 5, 2006, naming Dirk Johannes van den Boom as an inventor, entitled DETECTION AND QUANTIFICATION OF BIOMOLECULES USING MASS SPECTROMETRY. The entirety of this provisional patent application is incorporated herein, including all text and drawings.

BACKGROUND

Current methods for detecting and quantifying nucleic acids in multiplexed assays are limited, especially those assays that utilize fluorescent dyes for detection. For example, White discusses the problems of multiplexing using the TaqMAN® assay (*Trends in Biotechnology* (1996) 14(12); 478-483). Among other issues, fluorescent dyes offer only limited multiplexing options, and currently available methods that attempt to overcome these limitations, for example, by using primer-extension and ligation-based SNP analysis followed by universal PCR and hybridization to chip arrays are often very time consuming (e.g., 1-2 days).

The use of mass spectrometry offers a solution for improved multiplexing because of the increased number of detection channels, but the practical utility of previously disclosed mass spectrometry-based methods can be further improved. For example, the use of high-specificity hybridization of peptide nucleic acid (PNA) probes to PCR-amplified DNA and subsequent detection by mass spectrometry is described by Ross (*Anal. Chem.* (1997) 69:4197). Also, a primer extension method and detection of the primer extension product by mass spectrometry is described by Haff (Nucleic Acids Res. (1997) 25:3749). Additional mass spectrometry-based methods are described by Jurinke et al (*Adv Biochem Eng Biotechnol* (2002) 77:57-74).

SUMMARY

The invention in part provides methods for identifying and quantifying a target biomolecule, such as nucleic acid, and for detecting a target biomolecule sequence, such as a nucleic acid sequence or nucleotide sequence. Methods of the invention are advantageous for detecting multiple target nucleic acids simultaneously in a single sample or multiple samples while avoiding post-PCR enzymatic processes. Large sets of unique, mass-distinguishable products (MDP's) can be generated that allow for the simultaneous detection of multiple target nucleic acids. As described further herein, one or more target nucleic acids are amplified by standard amplification methods wherein the amplification process cleaves and degrades detector probes, which yield specific mass-distinguishable products detectable by mass spectrometry. Detection of multiple MDP's allows for the identification and/or quantification of multiple target nucleic acids.

Each mass-distinguishable product (MDP) has a unique physical characteristic that allows it to be uniquely identified when compared to other mass-distinguishable products used in the same assay. The mass-distinguishable products can be separated and identified based on this difference. For example, MDP's can differ from each other based on their unique, predetermined mass and be detected by mass spectrometry. Thus, mass spectrometric analysis reveals the presence of the target nucleic acid indirectly through the mass-distinguishable product.

The invention therefore in part provides a method of detecting, and optionally quantifying, a target nucleic acid sequence in an amplification reaction, the method comprising: providing a set of oligonucleotide primers, wherein a first primer contains a sequence complementary to a region in one strand of the target nucleic acid sequence, and a second primer contains a sequence complementary to a region in a second strand of the target nucleic acid sequence; providing at least one detector oligonucleotide containing a sequence complementary to a region of the target nucleic acid, wherein said detector oligonucleotide anneals within the target nucleic acid sequence bounded by the oligonucleotide primers in the first step, thereby creating an annealed duplex, and further wherein each oligonucleotide primer is selected to anneal to its complementary template upstream of any detector oligonucleotide annealed to the same nucleic acid strand; amplifying the target nucleic acid sequence employing an enzyme having 5' to 3' nuclease activity as a template-dependent polymerizing agent under conditions which are permissive for amplification cycling steps of (i) annealing of oligonucleotide primers and detector oligonucleotide to a template nucleic acid sequence contained within the target sequence, and (ii) extending the primer oligonucleotide wherein said nucleic acid amplification enzyme synthesizes a primer extension product while the 5' to 3' nuclease activity of the nucleic acid amplification enzyme simultaneously releases MDP's from the annealed duplexes comprising detector oligonucleotides and its complementary template nucleic acid sequences, thereby creating one or more MDP's; and detecting the one or more MDP's by mass spectrometry, thereby determining the presence or absence of the target sequence in a sample. Typically, the amplification reaction is a polymerase chain reaction. The amplification reaction can also be a multiplex reaction in which multiple targets are identified. In a related embodiment more than 2, 3, 4, 5, 6, 7, 8, 9, 10, 15, 20, 25, 30, 40, 50, 60, 70, 80, 90, 100, 150, 200, 300, 400, 500, 600, 700, 800, 900, 1000, and all numbers in between, or more target nucleic acids are detected in a single, multiplexed reaction. In another embodiment, more than one detector oligonucleotide is used to detect more than one target nucleic acid in a multiplexed reaction.

In some embodiments, a plurality of polymorphisms, such as single nucleotide polymorphisms (SNP's), or genes can be simultaneously determined by combining target nucleic acids with a pair of reagents under conditions of target amplification. Each pair of reagents includes an oligonucleotide primer which binds to target nucleic acid and a detector oligonucleotide, which may or may not be modified. In the case of SNP genotyping, the detector oligonucleotide binds to the site of the SNP and the oligonucleotide has a detection feature that is detectable upon its subsequent release. In a preferred embodiment, the detection feature is detectable by mass spectrometry. In the case of gene expression analysis, the detector oligonucleotide binds to gene-specific sequence and the oligonucleotide has a detection feature that is detectable upon its subsequent release. The conditions of sequence amplification can employ a polymerase having 5'-3' nuclease activity, dNTPs and auxiliary reagents to permit efficient sequence amplification. Examples of auxiliary reagents include, but are not limited to, betain, DMSO for CG-rich regions, detergents, and pyrophosphatases. The sequence amplification is performed, whereby detector oligonucleotides bound to the target nucleic acid are cleaved and/or degraded, released and subsequently detected by mass spectrometry. By having each SNP or gene associated with a specific MDP, one can determine the SNP's or genes present in a sample.

In another related embodiment, a polymerase chain reaction (PCR) amplification method of detecting a target nucleic acid sequence in a sample is provided, which comprises the steps of: providing to a PCR reaction containing the sample, a set of oligonucleotide primers, wherein a first PCR primer contains a sequence complementary to a region in one strand of the target nucleic acid sequence, and a second PCR primer contains a sequence complementary to a region in a second strand of the target nucleic acid sequence; providing at least one detector oligonucleotide containing a sequence complementary to a region of the target nucleic acid, wherein said detector oligonucleotide anneals within the target nucleic acid sequence bounded by the PCR primers of the first step, thereby creating an annealed duplex, and further wherein each PCR primer is selected to anneal to its complementary template upstream of any detector oligonucleotide annealed to the same nucleic acid strand; amplifying the target nucleic acid sequence employing a nucleic acid polymerase enzyme having 5' to 3' nuclease activity as a template-dependent polymerizing agent under conditions which are permissive for PCR cycling steps of (i) annealing of primers and detector oligonucleotide to a template nucleic acid sequence contained within the target sequence, and (ii) extending the primer wherein said nucleic acid polymerase enzyme synthesizes a primer extension product while the 5' to 3' nuclease activity of the nucleic acid polymerase enzyme simultaneously releases MDP's from the annealed duplexes comprising detector oligonucleotides and its complementary template nucleic acid sequences, thereby creating one or more MDP's; and detecting the one or more MDP's by mass spectrometry, thereby determining the presence or absence of the target sequence in the sample. In another embodiment, conditions which are permissive for PCR cycling may optionally include denaturation of the strands.

The invention also in part provides a method of detecting a target nucleic acid, comprising the steps of: annealing an oligonucleotide primer to the target nucleic acid, annealing a detector oligonucleotide to the same target nucleic acid; introducing an enzyme to extend the oligonucleotide primer in the direction of the detector oligonucleotide, wherein the enzyme cleaves and thereby releases at least a portion of the detector oligonucleotide, thereby producing one or more MDP's; and detecting the one or more MDP's by mass spectrometry. In a related embodiment, a portion of the detector oligonucleotide may be partially cleaved and therefore disassociate from the target nucleic acid. Thus, in this embodiment, the MDP's may include a partially cleaved detector oligonucleotide that disassociates from the target nucleic acid, and is subsequently detected by mass spectrometry. In another embodiment, a second oligonucleotide is introduced that binds to the synthesis product of the first oligonucleotide, whereby exponential amplification can subsequently occur. In a related embodiment, the target nucleic acid is initially a single-stranded nucleic acid molecule, for example cDNA.

The invention also in part provides non-amplification-based methods of detecting a target nucleic acid sequence in a sample, comprising the steps of: contacting a sample comprising a target nucleic acid with an (i) oligonucleotide primer, comprising a 3' end and a 5' end, and containing a sequence complementary to a region of the target nucleic acid and a (ii) detector oligonucleotide, comprising a 3' end and a 5' end, and containing a sequence complementary to a second region of the target nucleic acid sequence, thereby creating a (iii) mixture of duplexes under hybridization conditions, wherein the duplexes comprise the target nucleic acid annealed to the oligonucleotide primer and to the detector oligonucleotide such that the 3' end of the oligonucleotide primer is upstream of the 5' end of the detector oligonucleotide; exposing the sample from the first step to a cleavage agent under conditions sufficient to cleave and release the annealed detector oligonucleotide or at least one fragment thereof, thereby creating one or more MDP's; and detecting the one or more MDP's by mass spectrometry, thereby detecting the presence or absence of the target nucleic acid sequence in the sample.

The invention further provides, in part, a method of detecting a target nucleic acid, comprising the steps of: annealing a detector oligonucleotide to the target nucleic acid; introducing a cleavage agent to cleave at least a portion of the detector oligonucleotide; and detecting the partially cleaved detector oligonucleotide or fragments thereof by mass spectrometry.

In some embodiments, the reaction conditions allow for the extension of the oligonucleotide primers, which displaces and degrades the detector oligonucleotide, thereby yielding oligonucleotide fragments and/or any detection feature attached thereto. In some embodiments, the target nucleic acid is amplified prior to the detection method by an amplification reaction. In another embodiment, all of the steps prior to detection are performed simultaneously in a single, closed reaction vessel. In another embodiment, the amplifying or extending step of the method is repeated until a signal is detected. In a related embodiment, the number of amplifying steps is determined.

In certain embodiments, the detector oligonucleotide is introduced at a higher concentration relative to the oligonucleotide primer or primers. Also, in some instances, the detector oligonucleotide may be non-extendable by an enzyme. In another embodiment, more than one detector oligonucleotide is used to detect a single target nucleic acid, or more than one detector oligonucleotide anneals within the target nucleic acid sequence bounded by the oligonucleotide primers.

In some embodiments, the cleavage agent is an enzyme. In some embodiments, the enzyme has 5' to 3' nuclease activity. In other embodiments the enzyme has polymerase activity capable of amplifying target nucleic acid. In some embodiments, the enzyme is a DNA polymerase, and in other embodiments the enzyme is an RNA dependent DNA polymerase, a DNA dependent RNA polymerase, RNA dependent RNA polymerase or DNA dependent DNA polymerase. Exemplary DNA polymerases include Taq polymerase and *E. coli* DNA polymerase I. In another embodiment, the enzyme is thermostable.

The invention in part provides for the creation of MDP's resulting from the displacement and/or degradation of detector oligonucleotides. In one embodiment, more than one mass-distinguishable product (MDP) from the same detector oligonucleotide is detected by mass spectrometry, which creates a mass-specific detection signature that corresponds to a target nucleic acid. In another embodiment, the detector oligonucleotide comprises a sequence of nucleotides which is non-complementary to the target nucleic acid. The non-complementary region may be at the 5' end of the detector oligonucleotide, in the middle of the detector oligonucleotide, in which case the detector oligonucleotide is still capable of annealing to the target nucleic acid, or at the 3' end of the detector oligonucleotide. In other embodiments, the MDP's are capable of binding to a solid support upon release. For example, the MDP's may bind directly to a matrix for MALDI-TOF mass spectrometry analysis. In another embodiment, the one or more MDP's are amplified after their release, for example, by using a universal primer system.

In some embodiments, detector oligonucleotides are incorporated into a nucleic acid detection method that utilizes universal primers to amplify sequence-specific primers or oligonucleotides resulting from enzymatic modifications, wherein the amplification process yields mass-distinguishable products detectable by mass spectrometry. More specifically, an embodiment of the invention includes providing a plurality of target nucleic acid sequences each comprising from 3' to 5' a first, second and third target domain, the first target domain comprising a detection position, the second target domain being at least one nucleotide, contacting the target nucleic acid sequences with sets of probes for each target sequence, each set comprising: a first probe comprising from 5' to 3', a first domain comprising a first universal priming sequence, a second domain comprising a detector oligonucleotide binding domain and a third domain comprising a sequence substantially complementary to the first target domain of a target sequence, and an interrogation position within the 3' four terminal bases, a second probe comprising a first domain comprising a sequence substantially complementary to the third target domain of a target sequence, to form a set of first hybridization complexes, and a second domain comprising a second universal priming sequence, contacting the first hybridization complexes with at least a first universal primer that hybridize to the first universal priming sequence, an extension enzyme and dNTPs, under conditions whereby if the base at the interrogation positions are complementary with the bases at the detection positions, extension of the first probes occurs through the second target domains to form second hybridization complexes, contacting the second hybridization complexes with a ligase to ligate the extended first probes to the second probes to form amplification templates. The embodiment further includes introducing detector oligonucleotides, wherein specific detector oligonucleotides anneal to the sequence-specific amplification templates, introducing an enzyme to amplify the amplification templates, and detecting the one or more MDP's resulting from the amplification reactions, wherein determining the presence or absence of the target nucleic sequences. In another embodiment, the methods of the present invention are utilized in conjunction with the methods disclosed in U.S. Pat. No. 6,797,470; U.S. Pat. No. 6,890,741, U.S. Pat. No. 6,812,005, U.S. Pat. No. 6,890,741, US Patent Application Publication No. 20020006617, US Patent Application Publication No. 20030036064, US Patent Application Publication No. 20030104434, US Patent Application Publication No. 20030211489, US Patent Application Publication No. 20030108900, US Patent Application Publication No. 20030170684, US Patent Application Publication No. 20040121364, US Patent Application Publication No. 20040224352, US Patent Application Publication No. 20040224352, all of which are hereby incorporated by reference.

In some embodiments, the detector oligonucleotide is not modified, in which case unmodified MDP's comprising oligonucleotide fragments are detected by mass spectrometry. In other embodiments, the detector oligonucleotide comprises one or more nucleoside modifications. Nucleoside modifications include modifications to a nucleotide, phosphate backbone or sugar moiety. The nucleoside modification may occur in a non-complementary region of the detector oligonucleotide, at the 5' end of the detector oligonucleotide, at the 3' end of the detector oligonucleotide, or in the middle of the detector oligonucleotide, which ensures target-specific hybridization of the detector oligonucleotide to the target nucleic acid. In another embodiment, the nucleoside modification is selected from the group consisting of isotopic enrichment, isotopic depletion and halogen modification. In another embodiment, isotopic coding is achieved by the introduction of deuterium, or other suitable isotopes.

In certain embodiments, the detector oligonucleotide comprises one or more cleavage recognition sites. In another embodiment, the detector oligonucleotide comprises one or more non-degradable nucleotides. In yet another embodiment, the detector oligonucleotide comprises one or more cleavage recognition sites and one or more non-degradable nucleotides.

In a preferred embodiment, the detector oligonucleotide comprises one or more locked nucleic acids (LNAs), which serve as non-degradable nucleotides and thereby control the point of cleavage. LNAs bind very stably with their complement and have a highly reduced rate of cleavage relative to a nascent deoxynucleotide. This effect may be further enhanced by placing two or LNAs adjacent to each other. Additionally, LNAs increase the melting temperature of the oligonucleotides of which they are incorporated. The cleavage site for the mass degradation products are thus controlled for predictability of product size and proper identification.

In another embodiment, the detector oligonucleotide comprises one or more peptide nucleic acids (PNAs).

In some embodiments, the detector oligonucleotide comprises one or more detection moieties. In one embodiment, the detection moiety may be any one or more of a compomer, sugar, peptide, protein, antibody, chemical compound (e.g., biotin), mass tag (e.g., metal ions or chemical groups), fluorescent tag, charge tag (e.g., such as polyamines or charged dyes) and hydrophobic tag. In a related embodiment, the detection moiety is a mass-distinguishable product (MDP) or part of an MDP detected by mass spectrometry. In a specific embodiment, the detection moiety is a fluorescent tag or label that is detected by mass spectrometry. In some embodiments, the detection moiety is at the 5' end of the detector oligonucleotide, the detection moiety is attached to a non-complementary region of the detector oligonucleotide, or the detection moiety is at the 5' terminus of the non-complementary sequence. In another embodiment, the detection moiety is incorporated into or linked to an internal nucleotide or to a nucleotide at the 3' end of the detector oligonucleotide. In yet another embodiment, one or more detection moieties are used either alone or in combination.

In certain embodiments, the detection moiety is a synthetic polymer or a biopolymer or some combination thereof, while in other embodiments, the detection moiety is any compound that may be detected by mass spectrometry. In particular embodiments, the detection moiety is a biopolymer comprising monomer units, wherein each monomer unit is separately and independently selected from any one or more of an amino acid, a nucleic acid, and a saccharide. Amino acids and nucleic acids are the preferred monomer units. Because each monomer unit may be separately and independently selected, biopolymer detection moieties may be polynucleic acids, peptides, peptide nucleic acids, oligonucleotides, and so on.

In some embodiments, the detection moiety is a synthetic polymer, such as polyethylene glycol, polyvinyl phenol, polypropylene glycol, polymethyl methacrylate, and derivatives thereof. Synthetic polymers may typically contain monomer units selected from the group consisting essentially of ethylene glycol, vinyl phenol, propylene glycol, methyl methacrylate, and derivatives thereof. More typically the detection moiety may be a polymer containing polyethylene glycol units.

The invention in part provides detector oligonucleotides that serve as probes that bind to specific target nucleic acid sequences. In an embodiment, the detector oligonucleotide selectively binds to a gene-specific sequence, which thereby allows for gene expression analysis. In another embodiment, the detector oligonucleotide selectively binds to an allele-specific sequence. In a related embodiment, the allele-specific nucleotide base or bases of the detector oligonucleotide comprises a detection moiety or a nucleoside modification. In a preferred embodiment, the allele-specific nucleotide base or bases of the detector oligonucleotide fall in the middle or towards the 5' end of the detector oligonucleotide.

The invention also in part provides methods of detecting target nucleic acids based on epigenetic differences, such as methylation, acetylation and other non-sequence altering modifications. In one embodiment, the detector oligonucleotide selectively binds to a methylation-specific sequence based on the methylation status of the target nucleic acid. In a related embodiment, the detector oligonucleotide selectively binds to a methylation-specific sequence based on the methylation status of the target nucleic acid prior to bisulfite treatment, or, alternatively, after bisulfite treatment. In another embodiment, target nucleic acids are selectively enriched for methylated DNA (either before amplification or after amplification) by coating a container with a polypeptide capable of binding methylated DNA; contacting said polypeptide with a sample comprising methylated and/or unmethylated DNA; and detecting the binding of said polypeptide to methylated DNA. Methods for detecting methylated DNA are described in PCT Patent Publication No. WO06056478A1, which is hereby incorporated by reference.

The present invention in part provides methods for detecting a target nucleic acid. Generally, the method includes obtaining a plurality of detector oligonucleotides, each detector oligonucleotide designed specifically for a given assay (e.g., allele-specific, gene-specific, sequence-specific, methylation-specific, etc.), as described above. It is preferred that each detector oligonucleotide within the plurality is capable of yielding one or more unique mass-distinguishable products that correlate with the presence or absence of the target nucleic acid. By "unique mass-distinguishable product" it is meant that each detector oligonucleotide within the plurality will yield different mass-distinguishable product(s) from all other detector oligonucleotides in the plurality. A plurality will generally be understood to include two or more detector oligonucleotides. Next, the target molecule is contacted with the plurality of detector oligonucleotides under conditions suitable to allow for the generation of MDP's, which are analyzed by mass spectrometry. Typically, the mass is indicative of a specific target nucleic acid. In this way, the target molecule can be identified according to the unique combination of MDP's. Example 1 provides an example of a sequence-specific assay for the detection of exon 10 of the Rhesus D gene. In another example, an assay is designed for each particular SNP of a target nucleic acid, wherein the detector oligonucleotide of the assay yields unique MDP's depending on which SNP is present. If two SNP's are to be detected at a particular position, two allele-specific detector oligonucleotides with unique MDP's are used. For gene expression analysis, a gene-specific detector oligonucleotide and a competitor may be used. See, for example, US Patent Application No. 20040081993 (Cantor et al.), which is hereby incorporated by reference.

In some embodiments, the oligonucleotide primer selectively binds to an allele-specific sequence. In some embodiments, the 3' end of the oligonucleotide primer is at least one base upstream of the 5' end of the detector oligonucleotide.

The invention in part provides methods of detecting MDP's by mass spectrometry. In an embodiment, the detection is done by a mass spectrometer, which may be one of the following: MALDI-TOF MS, Tandem MS, ESI-TOF, ESI-iontrap, LC-MS, GC-MS, ion mobility MS, laser desorption ionization mass spectrometry (LDI-MS) and quadrupole-MS. Other mass spectrometry devices and methods now existing or which may be developed are within the scope of the present invention.

The invention also in part provides methods of detecting and quantifying biomolecules, such as target nucleic acids, wherein the generation of PCR product is monitored by detection of mass-distinguishable product (MDP). In one embodiment, the detection is done in real-time. In some embodiments, the detection in real-time is performed with an electrospray mass spectrometer or LC-MS. In another embodiment, the one or more MDP's are spotted at specific locations on a mass spectrometry-related medium that corresponds to a specific time during the amplification process. An example of a mass spectrometry-related medium is a matrix suitable for MALDI-TOF MS. In another embodiment, a competitor template nucleic acid is introduced, wherein the template nucleic acid serves as an internal control. In yet another embodiment, the number of amplification cycles is determined to obtain a quantitative result. The amount of starting target nucleic acid present in the reaction mixture may be quantified by cycle threshold (Ct), or any other method known in the art.

Also provided herein are methods for detecting a target nucleic acid sequence, which comprise analyzing a nucleic acid sample containing mass-distinguishable products by mass spectrometry, wherein the mass-distinguishable products result from (a) annealing an oligonucleotide primer to a target nucleic acid; (b) annealing a detector oligonucleotide to the same target nucleic acid; and (c) contacting the target nucleic acid with an enzyme that extends the oligonucleotide primer in the direction of the detector oligonucleotide, wherein: the detector oligonucleotide or portion thereof is complementary to the target nucleic acid sequence, and the enzyme cleaves and thereby releases at least a portion of the detector oligonucleotide, thereby producing one or more mass-distinguishable products; whereby the target nucleic acid sequence is detected by identifying the mass-distinguishable products by mass spectrometry. In certain embodiments, a second oligonucleotide is introduced that binds to the synthesis product of the first oligonucleotide, whereby exponential amplification can subsequently occur.

Provided also are methods for detecting a target nucleic acid sequence, which comprises analyzing a nucleic acid sample containing mass-distinguishable products by mass spectrometry, wherein the mass-distinguishable products result from (a) contacting a target biomolecule with a detectable probe containing an oligonucleotide that serves as a template nucleic acid under conditions in which the detectable probe specifically binds to the target biomolecule; (b) annealing an oligonucleotide primer to the template nucleic acid; (c) annealing a detector oligonucleotide to the same template nucleic acid; and (d) contacting the template nucleic acid with an enzyme that extends the oligonucleotide primer in the direction of the detector oligonucleotide, wherein: the detector oligonucleotide or portion thereof is complementary to the target nucleic acid sequence, and the enzyme cleaves and thereby releases at least a portion of the detector oligonucleotide, thereby producing one or more mass-distinguishable products; whereby the target nucleic acid sequence is detected by identifying the mass-distinguishable products by mass spectrometry. In certain embodiments, a second oligonucleotide is introduced that binds to the synthesis product of the first oligonucleotide, whereby exponential amplification can subsequently occur.

BRIEF DESCRIPTION OF THE DRAWINGS

FIG. 9 is a mass spectrogram showing the MDP's generated from the Exon5 specific detector oligonucleotide generated during PCR amplification (mass range between 2500 and 7000 Da). The mass signals at 5765 and 6335.9 Da represent remaining, unused PCR primer. The mass signals at 2741.6 Da and 3032.6 Da represent 5'MDP's containing the polyA tag (8 Adenine) cleaved at the first hybridized T nucleotide (AAAAAAAAT) and the polyA tag cleaved after the first two hybridized nucleotides (AAAAAATC). The Y-axis is signal intensity and the X-axis is mass to charge ratio.

DETAILED DESCRIPTION

Figure 1:
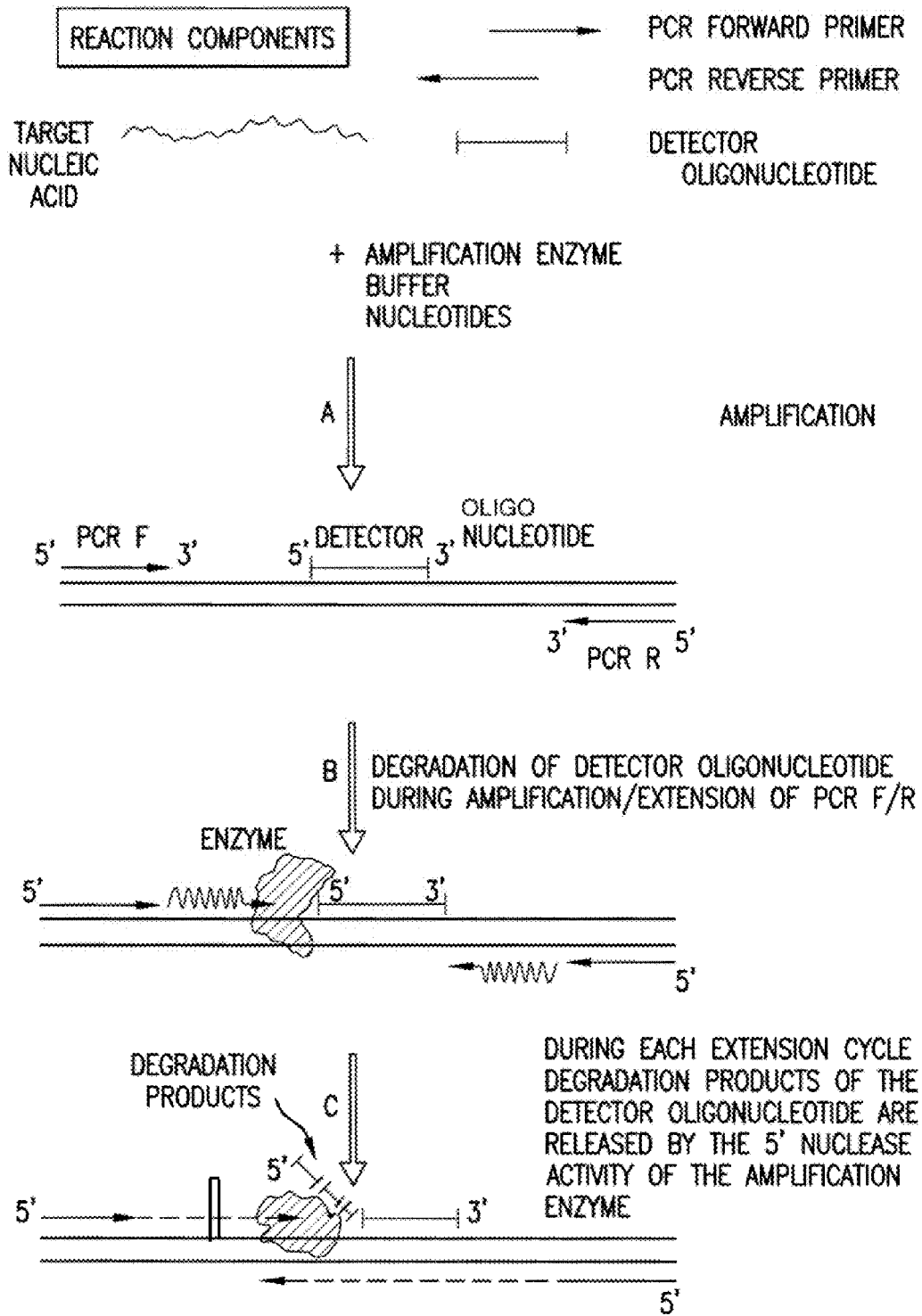
FIG. 1 is a schematic illustrating detection of a target nucleic acid using mass spectrometry. The reaction components include a target nucleic acid, forward and reverse PCR primers, a detector oligonucleotide, an amplification enzyme, and amplification reagents such as buffer(s) and nucleotides. In step A, extension of the primers occurs. During extension, the detector oligonucleotide is displaced and degraded (step B). During each amplification cycle, mass-distinguishable products (MDP's) (also referred to as degradation products in the Figure) are generated by the 5' nuclease activity of the enzyme (step C). Following amplification, MDP's may be optionally conditioned, and later detected by mass spectrometry. Reaction byproducts may include, inter alia, PCR product, leftover primers, undegraded oligonucleotide primers and MDP's (step D). Step E shows an exemplary spectrogram, where the y-axis is arbitrary intensity (a.i.) and the x-axis is mass (m) over z (charge). The presence of the MDP's confirms the presence of target nucleic acid.
Figure 1:
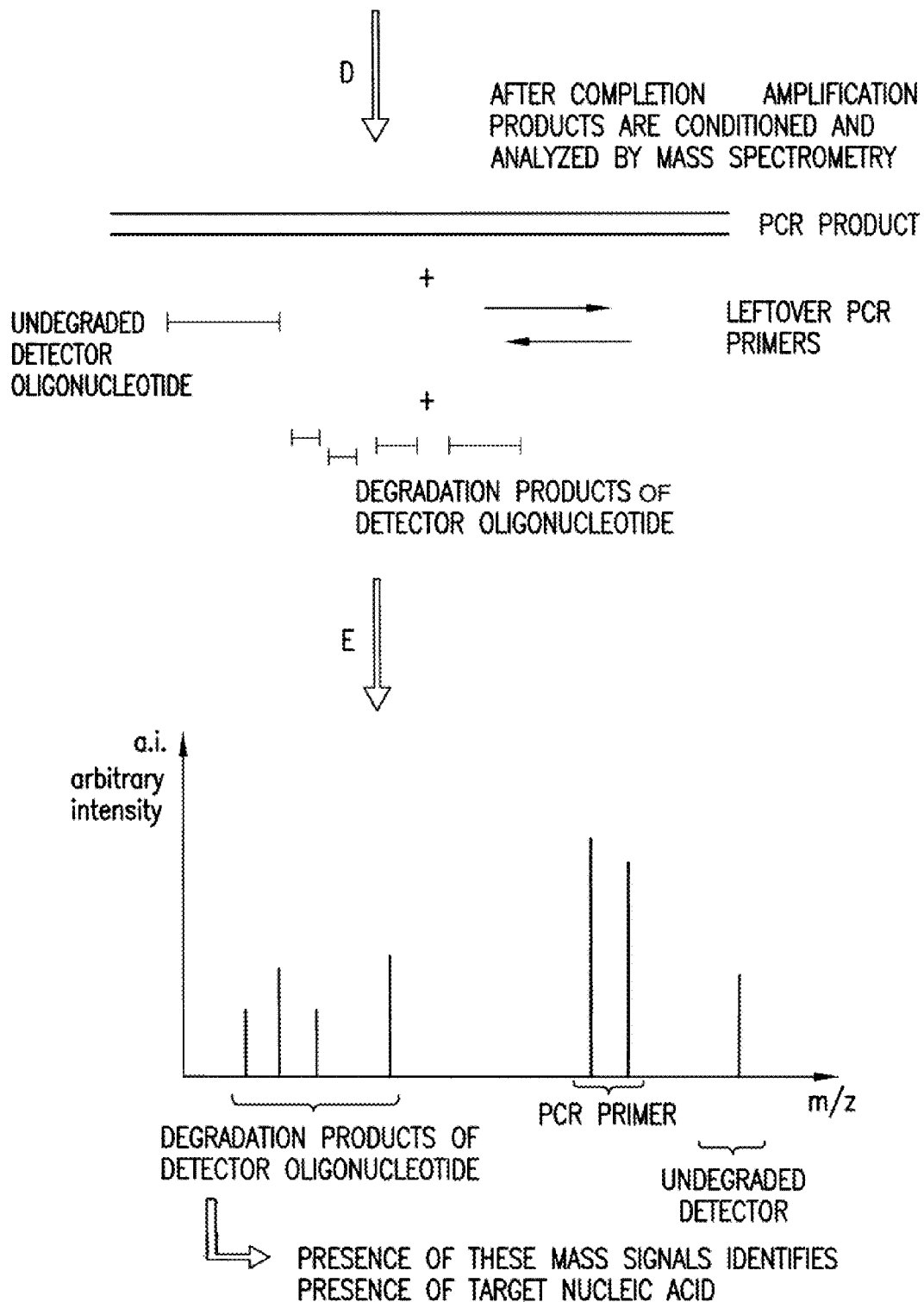
Figure 2:
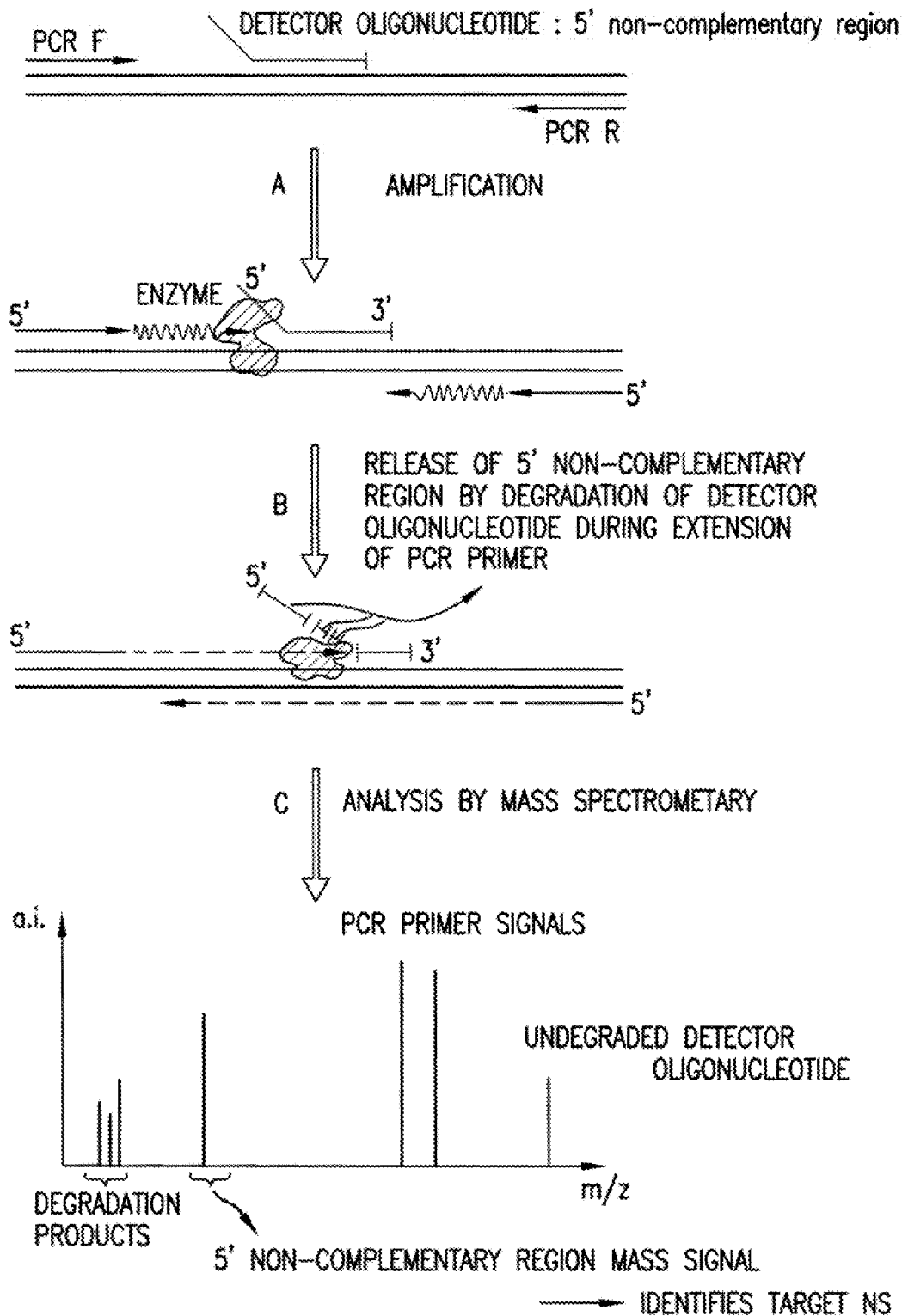
FIG. 2 is a schematic illustrating detection of a target nucleic acid using mass spectrometry, wherein the detector oligonucleotide comprises a 5' non-complementary region. In step B, the enzyme releases the 5' non-complementary region of the detector oligonucleotide, and it is detected in step C.
Figure 3:
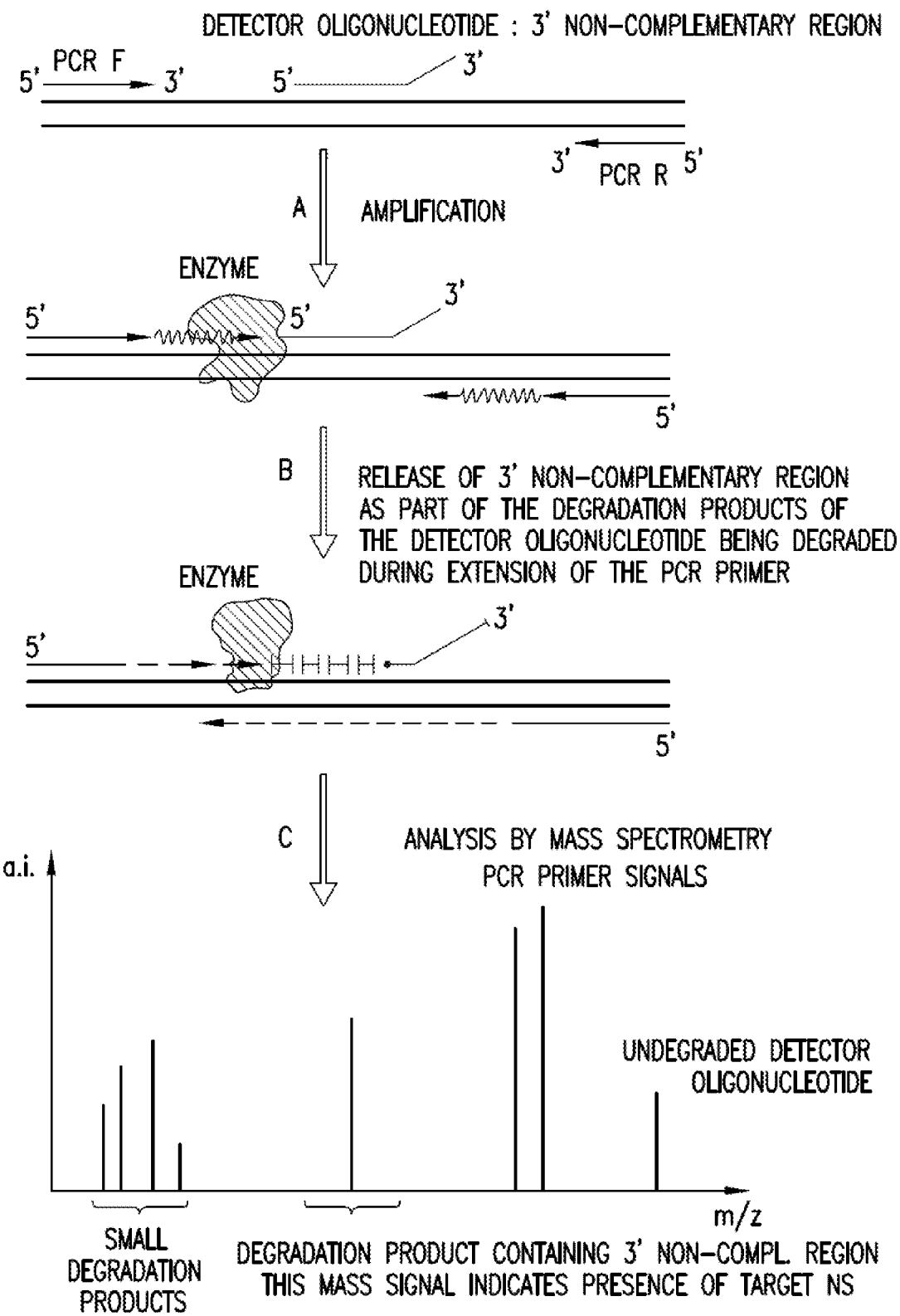
FIG. 3 is a schematic illustrating detection of a target nucleic acid using mass spectrometry, wherein the detector oligonucleotide comprises a 3' non-complementary region. In step B, the enzyme releases the 3' non-complementary region of the detector oligonucleotide, and it is detected in step C. The term "identifies target NS" at the bottom of the Figure refers to "identifies target nucleotide sequence." In one embodiment the invention in part may include a 3' non-complementary region that is cleaved and detected. In a further related embodiment the hybridized oligonucleotides upstream of the 3' non-complementary region are non-cleavable or non-degradable, thereby producing a unique defined cleavage product.
Figure 4:
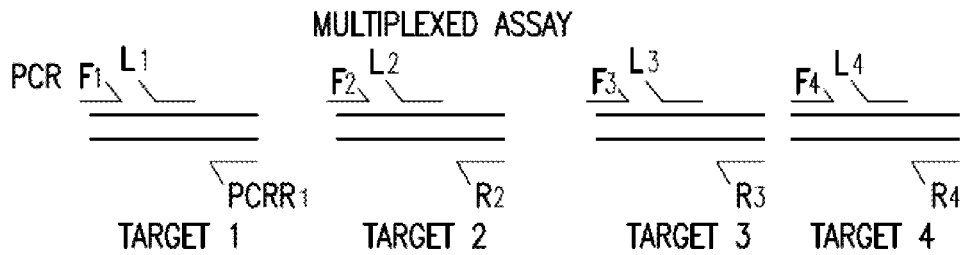
FIG. 4 is a schematic illustrating a multiplexed assay for detecting multiple target nucleic acids. An assay is designed for each target of the four targets (1-4), where each target has a unique detector oligonucleotide with a 5' non-complementary region of a specific length (L1-L4). Upon amplification (step A), the 5' non-complementary region MDP is generated if the target is present. In this particular example, targets 1 and 4 are present, so L1 and L4 MDP's are generated and detected by mass spectrometry (as illustrated in the spectrogram of step B).
Figure 4:
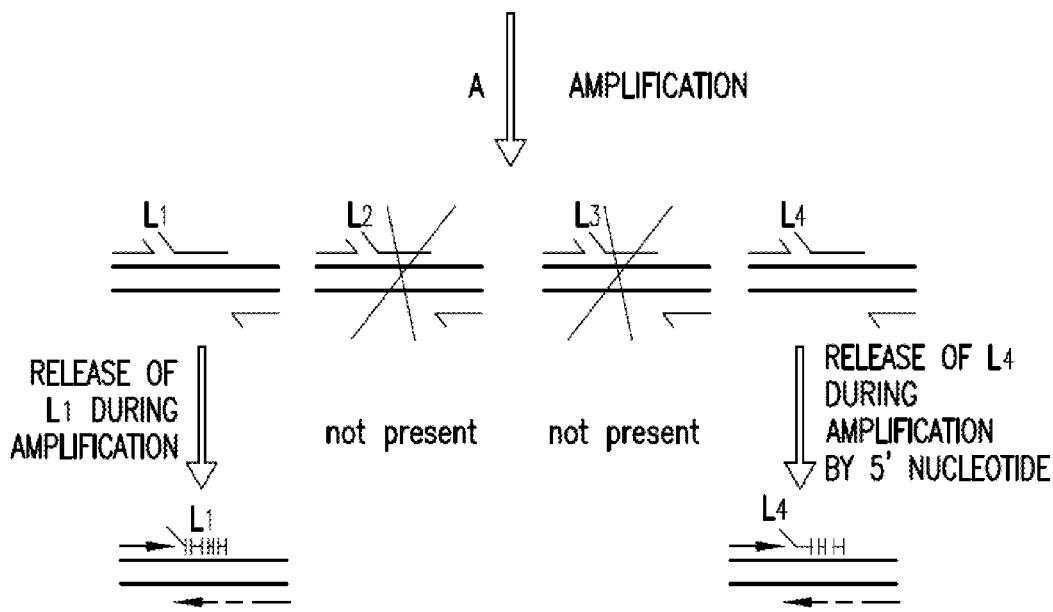
Figure 4:
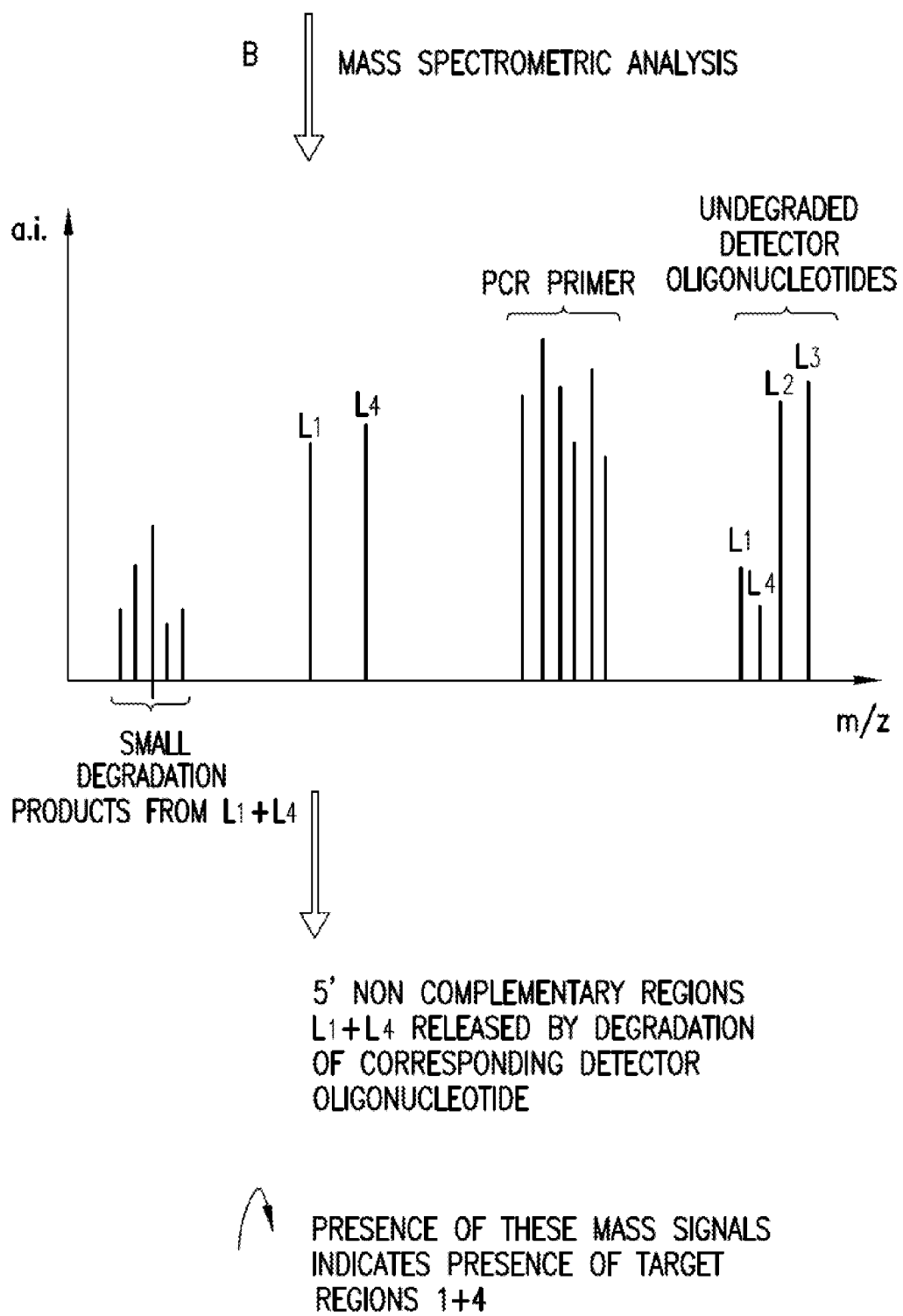
Figure 5:
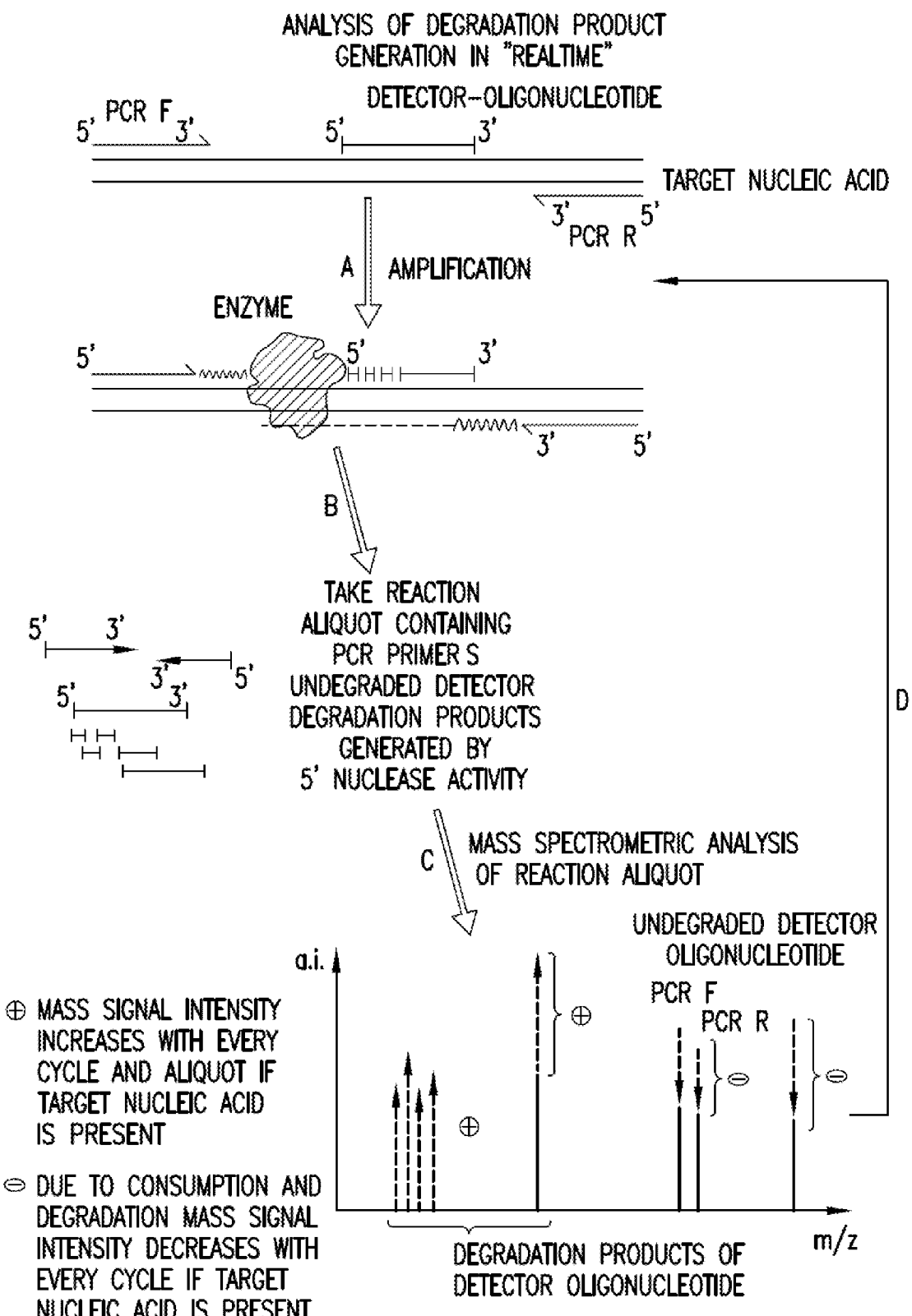
FIG. 5 is a schematic illustrating a real-time embodiment of the invention. The scheme is similar to that shown in FIG. 1, however, mass spectrometry analysis is performed after every cycle or at given time points (e.g., after every 5 cycles). If target nucleic acid is present, the degradation product (i.e., MDP) signal intensity increases with every cycle while the primer and undegraded detector oligonucleotide signal intensity decreases due to consumption and degradation.
Figure 6:
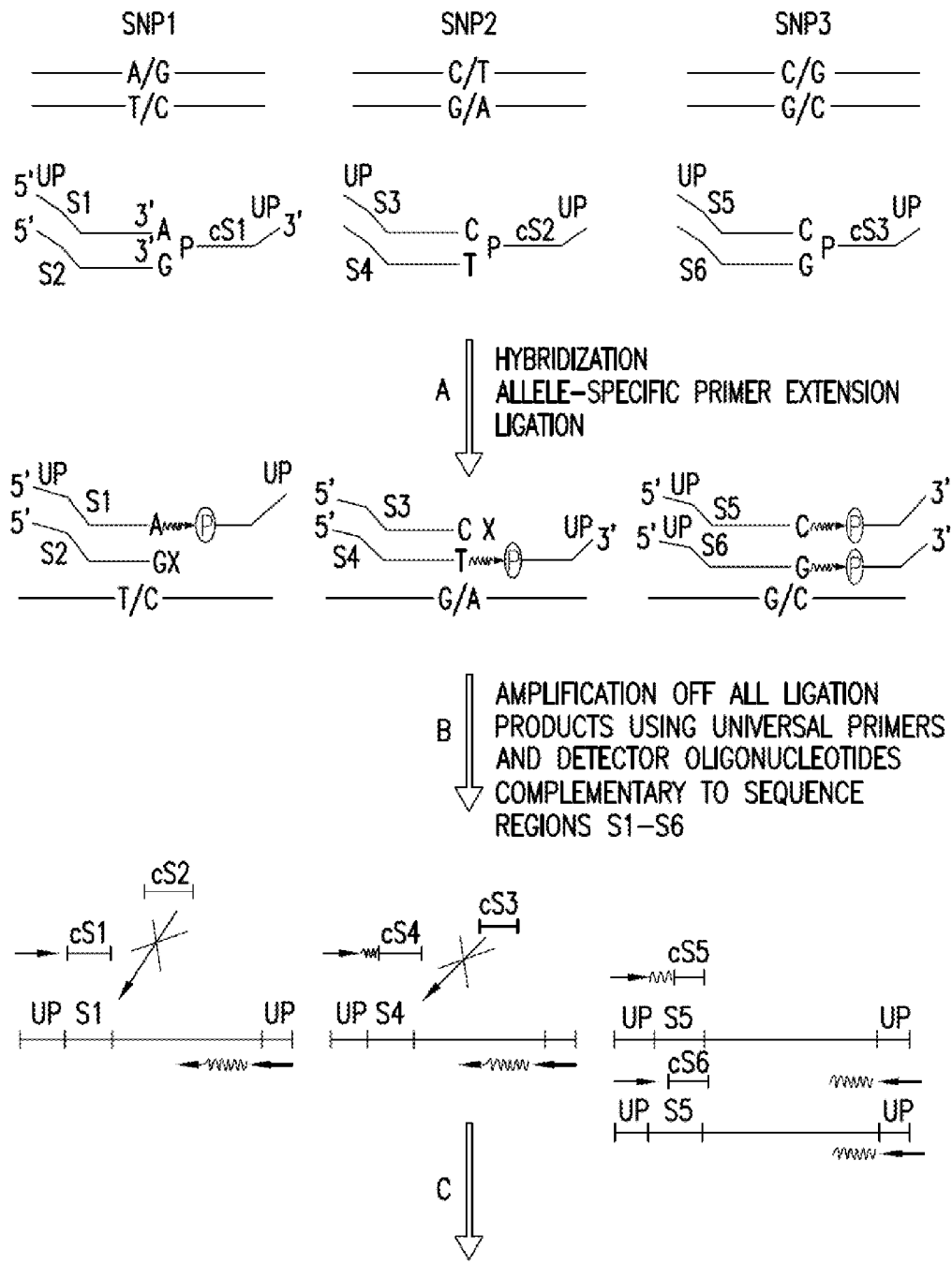
FIG. 6 is a schematic illustrating a variation of an assay in which universal primers are utilized to detect a target biomolecule. In this particular figure, a genotyping assay is shown where each single nucleotide polymorphism (SNP) has a unique set of primers. For example, SNP3 is assayed using allele-specific primers with sequence regions 5 and 6 (S5 and S6) corresponding to the C allele and G allele, respectively. A downstream primer is also introduced, designated CS3, or common primer3. In step A, the primers hybridize to the target, and allele-specific primer extension occurs if the allele is present. Upon extension, a ligation product forms. Detector oligonucleotides complementary to the assay-specific sequence regions of the ligation product are introduced, designated cS5 and cS6, or complementary primer5 and 6 for the SNP3 assay. Upon amplification of the ligation product using universal primers, the detector oligonucleotides (cS5 and cS6) are displaced and degraded to yield MDP's, which are detected by mass spectrometry. The exemplary mass spectrogram reveals the presence of allele A for SNP1, allele T for SNP2, and both alleles C and G (heterozygous) for SNP 3.
Figure 6:
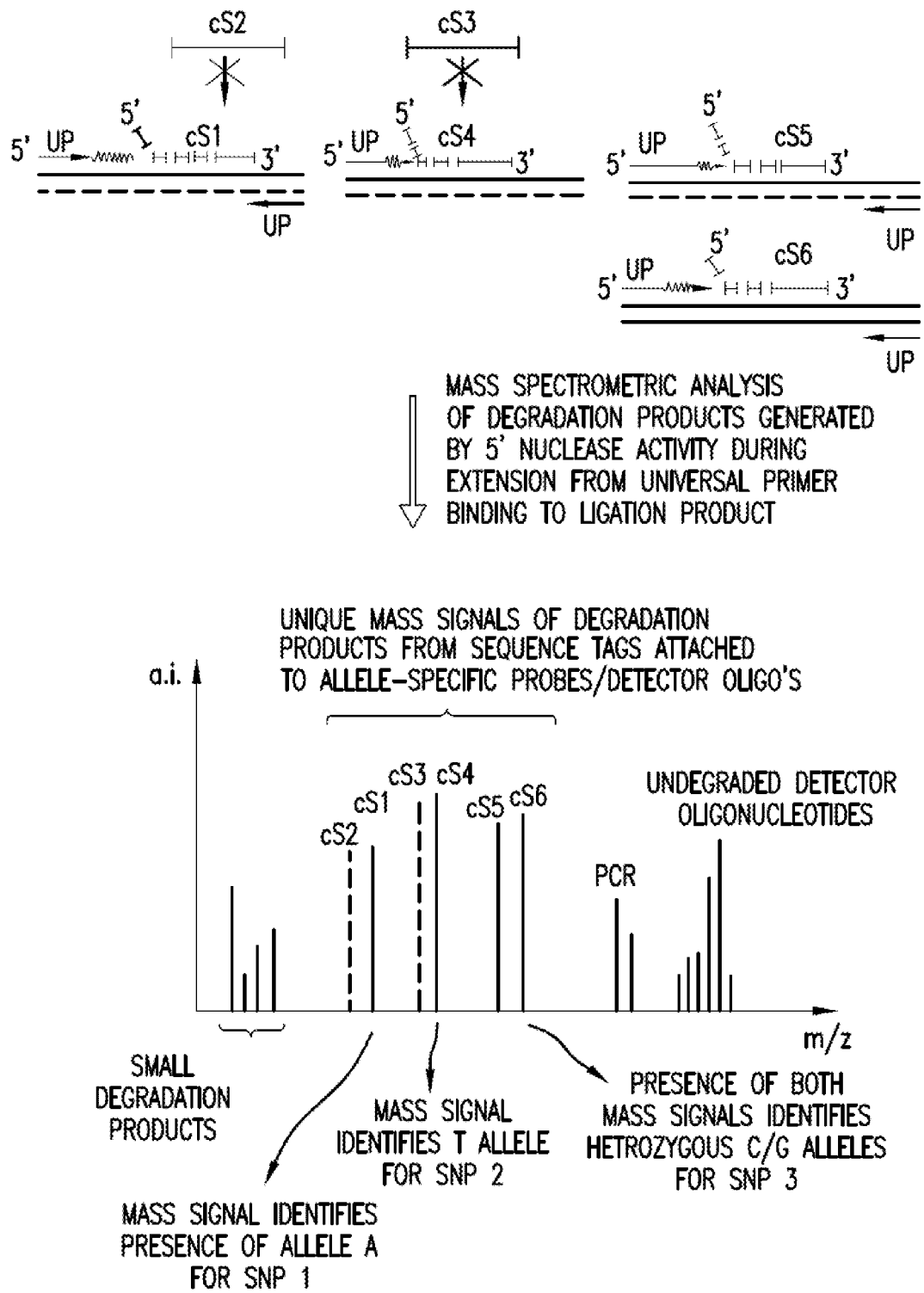
Figure 7:
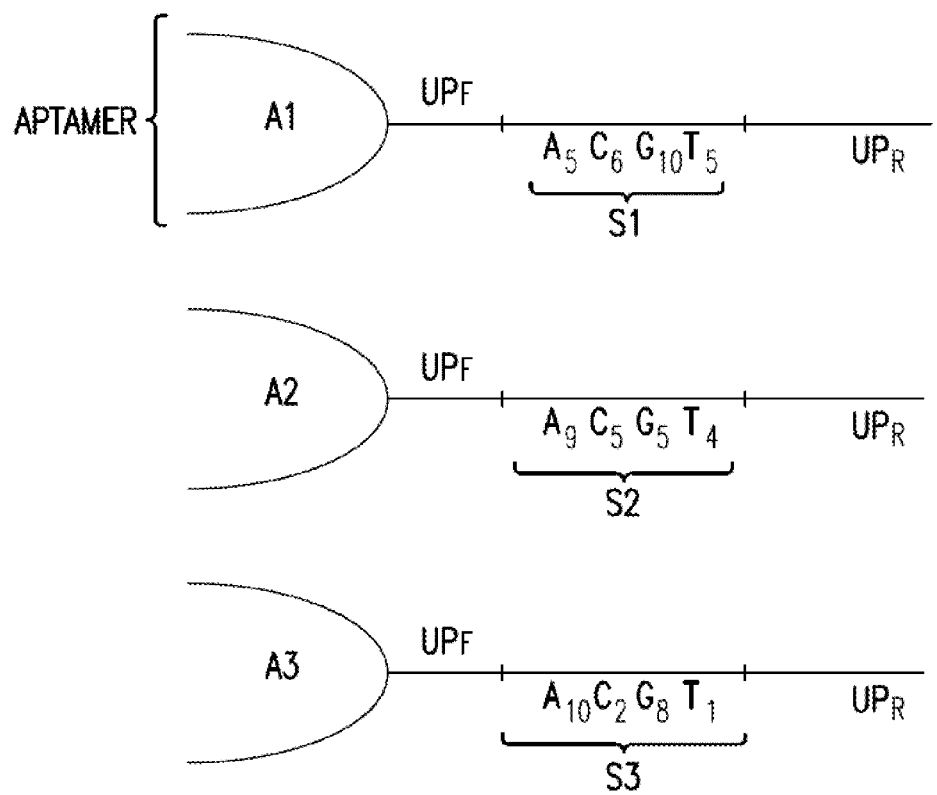
FIG. 7 is a schematic illustrating an embodiment of the invention useful for non-nucleic acid detection (e.g., protein detection). Each aptamer contains a target binding domain (A1-A3), a unique sequence (S) to which a unique complementary detector oligonucleotide (CS) can bind during subsequent amplification, and universal primer binding sites. In step A, target proteins bind to immobilized antibodies. In step B, non-binding reagents are removed by washing, and an aptamer library is added. Complementary aptamers bind to target proteins, and non-complementary aptamers are washed away. Universal primers and sequence-specific detector oligonucleotides are added (step C). Upon amplification, the detector oligonucleotides are displaced and degraded to yield MDP's, which are detected by mass spectrometry (step D). The presence of MDP1 and MDP3 indicate the presence of protein1 and protein3, respectively.
Figure 7:
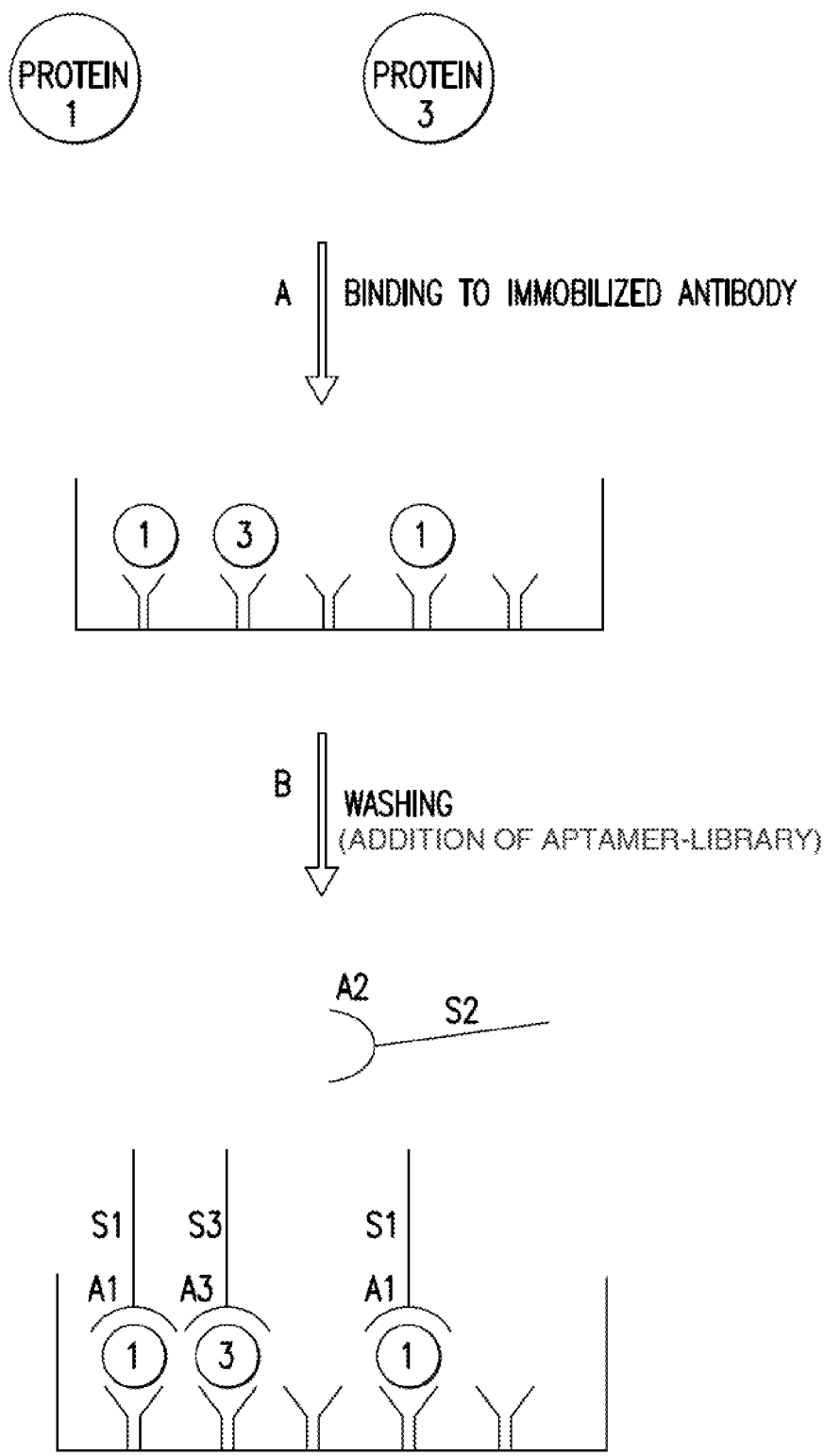
Figure 7:
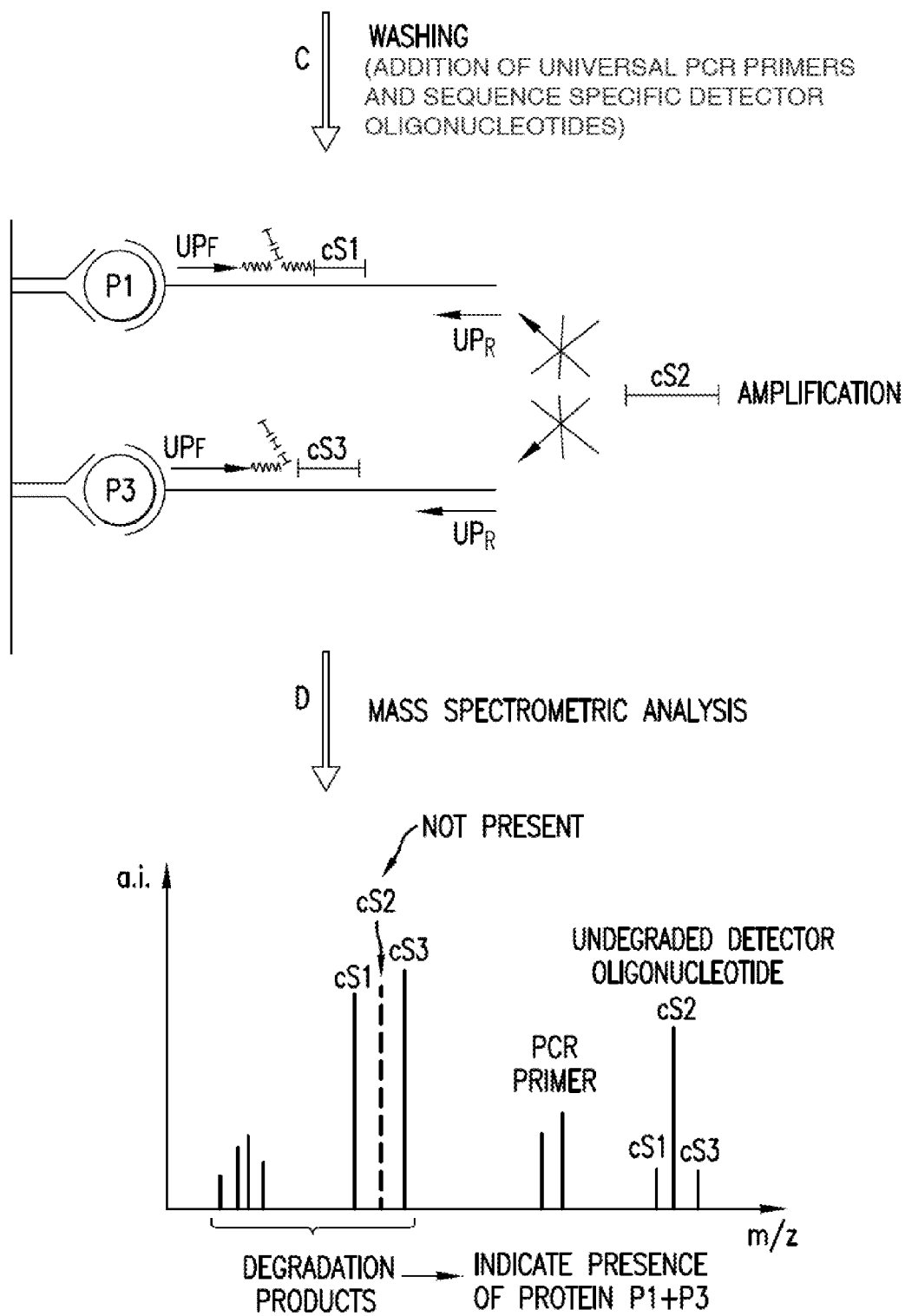

The present invention offers several advantages over current nucleic acid detection and quantification methods, such as increased multiplexing, assay simplicity, fast cycling times and no post PCR processing, for example. Current methods often require multi-step reactions including solid-phases purifications, transferring and washing steps, and post-PCR enzymatic reactions, all of which increase the total assay time and cost, thereby limiting the methods applicability. For example, TaqMan-based QPCR methods are limited by their use of dyes, whereas the present method is only limited by the number of unique detection features designed for each assay. This allows for the unambiguous detection of MDP's across a finite mass range.

The assay is also simple. In one embodiment, there is only one amplification or extension step, which occurs in a closed tube, so products are not transferred or subjected to a post-amplification enzymatic reaction. Also, the amplification step allows for fast cycling (i.e., the assay finishes in the plateau phase), so the speed and turn around time is only limited by the cycling speed—and fast cycles can be used. Finally, there is no post-amplification processing. For example, none of the products need to be captured on a solid support or bound to a capture probe and further manipulated by enzymes.

The invention provides an advantage of simultaneously identifying and quantifying large numbers of sequences from one or more samples for a range of applications, including, but not limited to, diagnostics, forensics and security applications such as identification of individuals (e.g., airline passengers). In certain applications, the invention provides the advantage of analyzing one or more samples for the presence or absence of multiple polymorphisms associated with a particular disease or diseases, to analyze the expression of one or more genes associated with a particular disease or diseases, or to identify the origin of one or more samples in a simple, fast multiplexed assay that can be done in hours rather than days.

Methods of the invention find utility in performing multiplexed assays for detection/analysis of biomolecule targets including, but not limited to nucleic acid detection, such as sequence recognition, SNP detection, transcription analysis or mRNA determination, allelic determination, mutation determination and methylation analysis. In another embodiment, the methods of the present invention may be used in combination with a proximity ligation or immunoassay-based method for the detection and quantification of non-nucleic acid biomolecules, such as proteins or peptides. For example, in one embodiment, a detector oligonucleotide of the invention is annealed to a ligated complex generated during an earlier proximity ligation reaction or immunoassay, which subsequently serves as a template for nucleic acid amplification reactions. Upon amplification of the ligation complex, mass-distinguishable products are created and detected as described herein, thus allowing for increased multiplexing. Proximity ligation and immunoassays are described further in U.S. Pat. No. 5,665,539; U.S. Pat. No. 6,511,809; U.S. Pat. No. 6,878,515; US Patent Application No. 20050233351; US Patent Application No. 20020064779; and by Roger Brent and his colleagues at the Molecular Sciences Institute (Berkeley, Calif.) in. *Nat. Methods.* 2005 January; 2(1):31-7, all of which are hereby incorporated by reference.

An advantage to using an amplification-based method that generates mass-distinguishable products detectable by mass spectrometry methods is the ability to simultaneously detect many target nucleic acids at the same time. Present methods are limited due to broad overlapping spectrums produced by existing fluorescent chromophore-based methods. Therefore, an upper limit for fluorescence multiplexing is most likely to be about ten different labels. Present mass spectrometry-based methods are useful for multiplexed reactions up to about 50-plexes. With the mass spectrometry-based method disclosed herein, multiplexing of greater than about fifty or hundreds, and perhaps even thousands, of different targets is possible. Due to this high level multiplexing ability, not only can many assays be used at the same time, any individual detector oligonucleotide can be labeled with many different detection features.

Finally, the assay has tremendous utility for any field that requires fast turnaround and multiplexing capabilities (e.g., public security). The assay is fast and robust, and the detection platform is small, highly accurate and easy-to-use, which makes the methods of the present invention ideal for a wide range of applications, including detection of infectious agents within a clinical sample, forensics, diagnostics, research (e.g., detection of a gene (cDNA) insert within a clone), security and field use.

A. DEFINITIONS

The term "sample" as used herein includes a specimen or culture (e.g., microbiological cultures) that includes nucleic acids. The term "sample" is also meant to include both biological and environmental samples. A sample may include a specimen of synthetic origin. Biological samples include whole blood, serum, plasma, umbilical cord blood, chorionic villi, amniotic fluid, cerebrospinal fluid, spinal fluid, lavage fluid (e.g., bronchioalveolar, gastric, peritoneal, ductal, ear, arthroscopic), biopsy sample, urine, feces, sputum, saliva, nasal mucous, prostate fluid, semen, lymphatic fluid, bile, tears, sweat, breast milk, breast fluid, embryonic cells and fetal cells. In a preferred embodiment, the biological sample is blood, and more preferably plasma. As used herein, the term "blood" encompasses whole blood or any fractions of blood, such as serum and plasma as conventionally defined. Blood plasma refers to the fraction of whole blood resulting from centrifugation of blood treated with anticoagulants. Blood serum refers to the watery portion of fluid remaining after a blood sample has coagulated. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The terms "target" or "target nucleic acid" as used herein are intended to mean any molecule whose presence is to be detected or measured or whose function, interactions or properties are to be studied. Therefore, a target includes essentially any molecule for which a detectable probe (e.g., detector oligonucleotide) or assay exists, or can be produced by one skilled in the art. For example, a target may be a biomolecule, such as a nucleic acid molecule, a polypeptide, a lipid, or a carbohydrate, that is capable of binding with or otherwise coming in contact with a detectable probe (e.g., an antibody), wherein the detectable probe also comprises nucleic acids capable of being detected by methods of the invention. As used herein, "detectable probe" refers to any molecule or agent capable of hybridizing or annealing to a target biomolecule of interest and allows for the specific detection of the target biomolecule as described herein. In one aspect of the invention, the target is a nucleic acid, and the detectable probe is a detector oligonucleotide. The terms "nucleic acid" and "nucleic acid molecule" may be used interchangeably throughout the disclosure. The terms refer to oligonucleotides, oligos, polynucleotides, deoxyribonucleotide (DNA), genomic DNA, mitochondrial DNA (mtDNA), complementary DNA (cDNA), bacterial DNA, viral DNA, viral RNA, RNA, message RNA (mRNA), transfer RNA (tRNA), ribosomal RNA (rRNA), siRNA, catalytic RNA, clones, plasmids, M13, P1, cosmid, bacteria artificial chromosome (BAC), yeast artificial chromosome (YAC), amplified nucleic acid, amplicon, PCR product and other types of amplified nucleic acid, RNA/DNA hybrids and polyamide nucleic acids (PNAs), all of which can be in either single- or double-stranded form, and unless otherwise limited, would encompass known analogs of natural nucleotides that can function in a similar manner as naturally occurring nucleotides and combinations and/or mixtures thereof. Thus, the term "nucleotides" refers to both naturally-occurring and modified/non-naturally-occurring nucleotides, including nucleoside tri, di, and monophosphates as well as monophosphate monomers present within polynucleic acid or oligonucleotide. A nucleotide may also be a ribo; 2'-deoxy; 2',3'-deoxy as well as a vast array of other nucleotide mimics that are well-known in the art. Mimics include chain-terminating nucleotides, such as 3'-O-methyl, halogenated base or sugar substitutions; alternative sugar structures including nonsugar, alkyl ring structures; alternative bases including inosine; deaza-modified; chi, and psi, linker-modified; mass label-modified; phosphodiester modifications or replacements including phosphorothioate, methylphosphonate, boranophosphate, amide, ester, ether; and abasic or complete internucleotide replacements, including cleavage linkages such a photocleavable nitrophenyl moieties.

The presence or absence of a target can be measured quantitatively or qualitatively. Targets can come in a variety of different forms including, for example, simple or complex mixtures, or in substantially purified forms. For example, a target can be part of a sample that contains other components or can be the sole or major component of the sample. Therefore, a target can be a component of a whole cell or tissue, a cell or tissue extract, a fractionated lysate thereof or a substantially purified molecule. Also a target can have either a known or unknown sequence or structure.

The term "amino acid" as used herein refers to naturally-occurring amino acid as well as any modified amino acid that may be synthesized or obtained by methods that are well known in the art.

The term "amplification reaction" refers to any in vitro means for multiplying the copies of a target sequence of nucleic acid.

"Amplifying" refers to a step of submitting a solution to conditions sufficient to allow for amplification. Components of an amplification reaction may include, but are not limited to, e.g., primers, a polynucleotide template, polymerase, nucleotides, dNTPs and the like. The term "amplifying" typically refers to an "exponential" increase in target nucleic acid. However, "amplifying" as used herein can also refer to linear increases in the numbers of a select target sequence of nucleic acid, but is different than a one-time, single primer extension step.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990.

"Oligonucleotide" as used herein refers to linear oligomers of natural or modified nucleosidic monomers linked by phosphodiester bonds or analogs thereof. Oligonucleotides include deoxyribonucleosides, ribonucleosides, anomeric forms thereof, peptide nucleic acids (PNAs), and the like, capable of specifically binding to a target nucleic acid. Usually monomers are linked by phosphodiester bonds or analogs thereof to form oligonucleotides ranging in size from a few monomeric units, e.g., 3-4, to several tens of monomeric units, e.g., 40-60. Whenever an oligonucleotide is represented by a sequence of letters, such as "ATGCCTG," it will be understood that the nucleotides are in 5'-3' order from left to right and that "A" denotes deoxyadenosine, "C" denotes deoxycytidine, "G" denotes deoxyguanosine, "T" denotes deoxythymidine, and "U" denotes the ribonucleoside, uridine, unless otherwise noted. Usually oligonucleotides comprise the four natural deoxynucleotides; however, they may also comprise ribonucleosides or non-natural nucleotide analogs. Where an enzyme has specific oligonucleotide or polynucleotide substrate requirements for activity, e.g., single stranded DNA, RNA/DNA duplex, or the like, then selection of appropriate composition for the oligonucleotide or polynucleotide substrates is well within the knowledge of one of ordinary skill.

As used herein "oligonucleotide primer", or simply "primer", refers to a polynucleotide sequence that hybridizes to a sequence on a target nucleic acid template and facilitates the detection of a detector oligonucleotide. In amplification embodiments of the invention, an oligonucleotide primer serves as a point of initiation of nucleic acid synthesis. In non-amplification embodiments, an oligonucleotide primer may be used to create a structure that is capable of being cleaved by a cleavage agent. Primers can be of a variety of lengths and are often less than 50 nucleotides in length, for example 12-25 nucleotides, in length. The length and sequences of primers for use in PCR can be designed based on principles known to those of skill in the art.

The term "detector oligonucleotide" as used herein refers to a polynucleotide sequence capable of hybridizing or annealing to a target nucleic acid of interest and allows for the specific detection of the target nucleic acid.

A "mismatched nucleotide" or a "mismatch" refers to a nucleotide that is not complementary to the target sequence at that position or positions. A detector oligonucleotide may have at least one mismatch, but can also have 2, 3, 4, 5, 6 or 7 or more mismatched nucleotides.

The term "polymorphism" as used herein refers to an allelic variant. Polymorphisms can include single nucleotide polymorphisms (SNP's) as well as simple sequence length polymorphisms. A polymorphism can be due to one or more nucleotide substitutions at one allele in comparison to another allele or can be due to an insertion or deletion, duplication, inversion and other alterations known to the art.

The term "mass-distinguishable product" as used herein may be used interchangeably with "cleavage product", "degradation product" or "probe fragment". In addition the acronym "MDP" may be used. The term "mass-distinguishable product" refers to the one or more degradation products resulting from the cleavage and release of the detector oligonucleotide as described by the methods herein. The mass-distinguishable products (MDP's) may include, but are not limited to, unmodified detector oligonucleotide fragments, modified detector oligonucleotide fragments (e.g., isotopically enriched or depleted oligonucleotide fragments), oligonucleotide fragments comprising detection moieties, detection moieties released from the detector oligonucleotide, and detector oligonucleotide fragments not complementary to the target nucleic acid. The mass-distinguishable products may also include partially cleaved detector oligonucleotides fragments that disassociate from the target nucleic acid upon partial degradation of the detector oligonucleotide.

The term "mass-specific detection signature" as used herein refers to the instance when more than one mass-distinguishable product is detected, thus resulting in a spectrogram with more than one mass peak per target nucleic acid. Upon cleavage of the detector oligonucleotide, multiple MDP's may be generated that are detectable by mass spectrometry. Each detection assay may have its own mass-specific detection signature comprising multiple cleavage products with different masses that correspond to the same target nucleic acid.

The term "modified" as used herein refers to a detector oligonucleotide that has been altered to include a detection feature.

The term "detection feature" as used herein refers to a modification that has been introduced to create a separation characteristic that is detectable, for example by a mass difference or a size difference, by mass spectrometry or any other size-based separation method such as gel electrophoresis (on a variety of supports including acrylamide or agarose gels, paper, etc.), chromatography or filtration. Separation characteristics allow for the detection of a specific MDP or subset of MDP's from a larger set of MDP's. Detection features include, but are not limited to, detection moieties and nucleoside modifications.

The term "detection moiety" as used herein refers to any atom or molecule that can be used to provide a detectable (preferably quantifiable) effect and that can be attached to or incorporated into a nucleic acid (e.g., detector oligonucleotide). In one preferred embodiment, the detection moiety is a moiety characterized by a unique mass, allowing specific identification in a mass-based separation, e.g., by mass spectrometry, gel electrophoresis, chromatography or filtration. Detection moieties include, but are not limited to, nucleotides, compomers, sugars, peptides, proteins and antibodies, chemical compounds, metal compounds, electron-absorbing substances, binding moieties such as biotin, mass tags, fluorescent tags, charge tags, volatile tags and hydrophobic tags. Additional examples of detection moieties that may be used in conjunction with the present invention are provided in U.S. Patent Publication No. 20030194717 (application Ser. No. 10/221,666), which is hereby incorporated by reference.

The term "compomer" as used herein is a molecule synthesized in a target detection assay from a compomer template to indirectly indicate the presence of a particular target molecule in a sample being assayed. Compomers are comprised of one or more subunits. Particularly preferred subunits for compomer polymerization are nucleobase subunits. Compomers are described in greater detail in US Patent Application 20050287533 (Ser. No. 10/874,898), which is hereby incorporated in its entirety by reference.

The term "nucleoside modification" as used herein refers to alterations of the detector oligonucleotide at the molecular level (e.g., base moiety, sugar moiety or phosphate backbone). Nucleoside modifications include, but are not limited to, the introduction of cleavage blockers or cleavage inducers, the introduction of minor groove binders, isotopic enrichment, isotopic depletion, the introduction of deuterium, and halogen modifications. Nucleoside modifications may also include moieties that increase the stringency of hybridization or increase the melting temperature of the detector oligonucleotide. For example, a nucleotide molecule may be modified with an extra bridge connecting the 2' and 4' carbons resulting in locked nucleic acid (LNA) nucleotide that is resistant to cleavage by a nuclease.

The term "specific" or "specificity" in reference to the binding of one molecule to another molecule, such as a probe for a target polynucleotide, refers to the recognition, contact, and formation of a stable complex between the two molecules, together with substantially less recognition, contact, or complex formation of that molecule with other molecules. As used herein, the term "anneal" refers to the formation of a stable complex between two molecules.

A probe is "capable of hybridizing" to a nucleic acid sequence if at least one region of the probe shares substantial sequence identity with at least one region of the complement of the nucleic acid sequence. "Substantial sequence identity" is a sequence identity of at least about 80%, preferably at least about 85%, more preferably at least about 90%, 95% or 99%, and most preferably 100%. For the purpose of determining sequence identity of a DNA sequence and a RNA sequence, U and T often are considered the same nucleotide. For example, a probe comprising the sequence ATCAGC is capable of hybridizing to a target RNA sequence comprising the sequence GCUGAU.

The term "cleavage agent" as used herein refers to any means that is capable of cleaving a detector oligonucleotide to yield mass-distinguishable products, including but not limited to enzymes. For methods wherein amplification does not occur, the cleavage agent may serve solely to cleave, degrade or otherwise release the detector oligonucleotide or fragments thereof. The cleavage agent may be an enzyme. The cleavage agent may be natural, synthetic, unmodified or modified.

For methods wherein amplification occurs, the cleavage agent is preferably an enzyme that possess synthetic (or polymerization) activity and nuclease activity. Such an enzyme is often a nucleic acid amplification enzyme. An example of a nucleic acid amplification enzyme is a nucleic acid polymerase enzyme such as *Thermus aquaticus* (Taq) DNA polymerase (TaqMAN®) or *E. coli* DNA polymerase I. The enzyme may be naturally occurring, unmodified or modified.

The term "polymerase" refers to an enzyme that catalyzes polynucleotide synthesis by addition of nucleotide units to a nucleotide chain using DNA or RNA as a template. The term refers to either a complete enzyme or a catalytic domain.

B. INTRODUCTION

The present invention pertains in part to quantitative amplification processes employing a hybridization probe to be detected by mass spectrometry and a reaction comprising a single enzyme capable of synthesis and nuclease activities. In contrast, certain quantitative amplification applications described elsewhere require (a) a hybridization probe containing a detectable label, for example a fluorescent tag, that is detected by a method other than mass spectrometry (see, e.g., U.S. Pat. No. 5,210,015), or (b) multiple cleavage agents employed to cleave a cleavage structure in a non-amplification based method (see, e.g., U.S. Pat. No. 5,719,028). In embodiments described herein, a detector oligonucleotide is included in the amplification reaction along with primers that amplify the template. Further, the detector oligonucleotide or fragments thereof are detected by mass spectrometry allowing for enhanced levels of multiplexing. In some embodiments, the detector oligonucleotide is modified and in other embodiments the detector oligonucleotide is unmodified. The amplification conditions, enzyme properties, detector oligonucleotide properties, detector oligonucleotide binding properties and mass-distinguishable product detection methods are described in further detail herein hereafter.

C. AMPLIFICATION CONDITIONS

In one embodiment, the methods described herein employ modified quantitative amplification methods that allow for accurate and sensitive nucleic acid analysis in a multiplexed manner. The polymerase chain reaction (PCR), as described in U.S. Pat. Nos. 4,683,195 and 4,683,202 to Mullis and Mullis et al., describe a method for increasing the concentration of a segment of target sequence in a mixture of genomic DNA without cloning or purification. PCR can be used to directly increase the concentration of the target to an easily detectable level. This process for amplifying the target sequence involves introducing a molar excess of two oligonucleotide primers which are complementary to their respective strands of the double-stranded target sequence to the DNA mixture containing the desired target sequence. The mixture is denatured and then allowed to hybridize. Following hybridization, the primers are extended with polymerase so as to form complementary strands. The steps of denaturation, hybridization, and polymerase extension can be repeated as often as needed, in order to obtain relatively high concentrations of a segment of the desired target sequence.

Methods of the present invention allow for the amplification reaction to be performed simultaneously in single, closed reaction vessel, wherein the amplification step may be repeated until a signal is detected. Byproducts of this synthesis are oligonucleotide fragments from the detector oligonucleotide which consist of a mixture of mono-, di- and larger nucleotide fragments. The detector oligonucleotide may be modified to include detection features detectable by mass spectrometry or the oligonucleotide fragments may be modified to yield mass-distinguishable products of a given molecular mass or size. Repeated cycles of denaturation, detector oligonucleotide and primer annealing, and primer extension and cleavage of the detector oligonucleotide result in the exponential accumulation of the target region defined by the primers and the exponential generation of mass-distinguishable products. Sufficient cycles are run to achieve a detectable species of MDP's.

The present invention offers many advantages including the ability to more easily design and perform multiplex assays, especially compared to assays currently available. In multiplex assays, several target nucleic acids can be detected simultaneously. In a multiplex format, sets of specially designed detector oligonucleotides are used such that the resulting mass-distinguishable products have a unique mass that can be differentiated from each other. A multiplex experiment can be used to detect 2 or more target nucleic acids, 10 or more target nucleic acids, 100 or more target nucleic acids, or 1,000 or more target nucleic acids in the same assay. The number of detector oligonucleotides used in a multiplex assay is equal to or greater than the number of target nucleic acids to be detected. For example, when a multiplex experiment is used to detect 10 target nucleic acids, 10 or more detector oligonucleotides that result in 10 or more mass-distinguishable products of unique mass are used. The number of analytes that can be detected in a single assay is limited only by the number of mass-distinguishable products that can be detected in a single assay. As described herein, mass spectrometry can resolve small differences in mass allowing the use of a large number of detector oligonucleotides in a single assay.

D. PRIMER PROPERTIES

Oligonucleotide primers and probes can be prepared using any suitable method, such as, for example, methods using phosphotriesters and phosphodiesters well known to those skilled in the art. In some embodiments, one or more detection moieties are included in the detector oligonucleotide. The oligonucleotide can also be modified at the base moiety, sugar moiety, or phosphate backbone, for example, with minor groove binders or intercalating agents.

The primers for the amplification reactions are designed according to known algorithms. The primers are designed to hybridize to sequences that flank the target nucleic acid. Typically, commercially available or custom software will use algorithms to design primers such that the annealing temperatures are close to melting temperature. Amplification primers are usually at least 12 bases, more often about 15, 18, or 20 bases in length. Primers are typically designed so that all primers participating in a particular reaction have melting temperatures that are within 5 degree C., and most preferably within 2 degree C. of each other. Primers are further designed to avoid priming on themselves or each other. Primer concentration often is sufficient to bind to the amount of target sequences that are amplified so as to provide an accurate assessment of the quantity of amplified sequence. Those of skill in the art will recognize that the concentration of primer will vary according to the binding affinity of the primers as well as the quantity of sequence to be bound. Typical primer concentrations will range from 0.01 µM to 1.0 µM. Also, the primer concentration may be altered relative to the detector oligonucleotide concentration, wherein the detector oligonucleotide concentration is greater than the primer concentration.

In another embodiment, the forward and reverse primer concentrations may be altered relative to each other (a condition sometimes referred to as Asymmetric PCR) to thereby to preferentially amplify one strand of the template DNA more than the other. In a preferred embodiment, the strand on which the detector oligonucleotide binds is preferentially amplified.

The amplification reactions are incubated under conditions in which the primers hybridize to the target sequence template and are extended by a polymerase. Such reaction conditions may vary, depending on the target nucleic acid of interest and the composition of the primer. The amplification reaction cycle conditions are selected so that the primers hybridize specifically to the target template sequence and are extended. Primers that hybridize specifically to a target template amplify the target sequence preferentially in comparison to other nucleic acids that may be present in the sample that is analyzed.

E. ENZYME PROPERTIES

The present invention incorporates the use of a cleavage agent to degrade and release detectable mass-distinguishable products. Several nucleases are known in the art that can be used to cleave different types of nucleic acids. For example, nucleases are available that can cleave double-stranded DNA, for example, DNAse I and Exonuclease III, or single-stranded DNA, for example, nuclease S1. Nucleases include enzymes that function solely as nucleases as well as multi-functional enzymes that contain nuclease activity such as, for example, DNA polymerases like Taq polymerase that have 5' nuclease activity. Several derivatives of Taq polymerases derived from different bacterial species or from designed mutations are known which cleave specific structures of nucleic acid hybrids (Kaiser et al., J. Biol. Chem. 274:21387-21394 (1999); Lyamichev et al., Proc. Natl. Acad. Sci. USA 96:6143-6148 (1999); Ma et al., J. Biol. Chem. 275:24693-24700 (2000)). For example, Cleavase™ enzymes (Third Wave Technologies) have been developed that cleave only at specific nucleic acid structures. In a preferred embodiment, the cleavage agent is an enzyme with polymerase and nuclease activity, wherein the target nucleic acid is exponentially amplified while mass-distinguishable products are generated.

In some embodiments, the enzyme cleaves the detector oligonucleotide one nucleotide into the 5' end of the detector oligonucleotide region that is hybridized to the target. In another embodiment, the detector oligonucleotide is not cleaved nucleotide-by-nucleotide. Instead, cleavage is regulated through the introduction of detection moieties or nucleoside modifications that yield mass-distinguishable products of greater than one nucleotide. In a preferred embodiment, a detector oligonucleotide is cleaved in such a way that it yields reproducible and distinguishable MDP's.

F. DETECTOR OLIGONUCLEOTIDE PROPERTIES

The detector oligonucleotides of the invention can be any suitable size, and are typically in the range of from about 6 to about 100 nucleotides, more preferably from about 6 to about 80 nucleotides and even more frequently from about 10 to about 40 nucleotides. The precise sequence and length of a detector oligonucleotide depends in part on the nature of the target polynucleotide to which it binds. The binding location and length may be varied to achieve appropriate annealing and melting properties for a particular embodiment. Guidance for making such design choices can be found in many art recognized references. Hybridization of the detector oligonucleotide, in conjunction with amplification of the target sequence with primers to amplify the target nucleic acid, provides a quantitative determination of the amount of the target nucleic acid sequence in a sample. In a preferred embodiment, the detector oligonucleotide is non-extendable (e.g., through the introduction of a 3' dideoxynucleotide), thereby reducing the probability of amplification artifacts.

The detector oligonucleotide may also contain a mismatch to the target nucleic acid sequence, e.g., at an invariant (non-polymorphic) position of the target nucleic acid sequence. In some embodiments, additional nucleotides, e.g., two, three, four, five, six, or seven or more nucleotides, can also be mismatched to the target nucleic acid. In some embodiments, the additional mismatches form a stem-loop structure with upstream detector oligonucleotide sequences prior to hybridization with the target nucleic acid sequence. The mismatch nucleotides may be present at the 5' end, 3' end or internal to the detector oligonucleotide. Examples of 3' mismatches are described in US Patent Application No. 20060024695, which is hereby incorporated by reference. In another embodiment, the 5' end of the complementary region of the detector oligonucleotide may contain a GC clamp.

Detector oligonucleotides may be modified or unmodified. Modified oligonucleotides may contain detection moieties or nucleoside modification. Examples of detection moieties and nucleoside modifications, and methods of making and using them, are described in U.S. Pat. No. 5,174,962; U.S. Pat. No. 5,360,819; U.S. Pat. No. 5,516,931; U.S. Pat. No. 6,268,129; U.S. Pat. No. 6,635,452; U.S. Pat. No. 6,322,980; U.S. Pat. No. 6,514,700; U.S. Pat. No. 6,649,351; and U.S. Pat. No. 6,613,509; and US Patent Application No. US 20060172319, all of which are hereby incorporated by reference.

The term "detection moiety" refers to a mass label, tag or signal. Examples of the types of detection moieties for the present invention include a repertoire of compounds, preferably ones that share similar mass spectrometric desorption properties and have similar or identical coupling chemistries in order to streamline synthesis of multiple detection moiety variants. A detection moiety of the present invention is detectable by mass spectrometry. Representative types of mass spectrometric techniques include matrix-assisted laser desorption ionization, direct laser-desorption, electrospray ionization, secondary neutral, and secondary ion mass spectrometry, with laser-desorption ionization being preferred. The dynamic range of mass spectral measurements can generally be extended by use of a logarithmic amplifier and/or variable attenuation in the processing and analysis of the signal.

In other related embodiments, the nucleotides can be labeled with any type of chemical group or moiety that allows for detection, cleavage, or cleavage resistance of the detector oligonucleotide including but not limited to radioactive molecules, fluorescent molecules, antibodies, antibody fragments, haptens, carbohydrates, biotin, derivatives of biotin, phosphorescent moieties, luminescent moieties, electrochemiluminescent moieties, chromatic moieties, and moieties having a detectable electron spin resonance, electrical capacitance, dielectric constant or electrical conductivity. The nucleotides can be labeled with one or more than one type of chemical group or moiety. Each nucleotide can be labeled with the same chemical group or moiety. Alternatively, each different nucleotide can be labeled with a different chemical group or moiety. The labeled nucleotides can be dNTPs, ddNTPs, or a mixture of both dNTPs and ddNTPs. The unlabeled nucleotides can be dNTPs, ddNTPs or a mixture of both dNTPs and ddNTPs.

Any combination of nucleotides can be used to incorporate nucleotides including but not limited to unlabeled deoxynucleotides, labeled deoxynucleotides, unlabeled dideoxynucleotides, labeled dideoxynucleotides, a mixture of labeled and unlabeled deoxynucleotides, a mixture of labeled and unlabeled dideoxynucleotides, a mixture of labeled deoxynucleotides and labeled dideoxynucleotides, a mixture of labeled deoxynucleotides and unlabeled dideoxynucleotides, a mixture of unlabeled deoxynucleotides and unlabeled dideoxynucleotides, a mixture of unlabeled deoxynucleotides and labeled dideoxynucleotides, dideoxynucleotide analogues, deoxynucleotide analogues, a mixture of dideoxynucleotide analogues and deoxynucleotide analogues, phosphorylated nucleoside analogues, 2'-deoxynucleotide-5'-triphosphate, and modified 2'-deoxynucleotide-5'-triphosphate.

All four nucleotides can be labeled with different fluorescent groups, which will allow one reaction to be performed in the presence of all four labeled nucleotides. Alternatively, four separate "fill in" reactions can be performed for each locus of interest; each of the four reactions will contain a different labeled nucleotide (e.g. ddATP*, ddTTP*, ddGTP*, or ddCTP*, where * indicates a labeled nucleotide). Each nucleotide can be labeled with different chemical groups or the same chemical groups. The labeled nucleotides can be dideoxynucleotides or deoxynucleotides.

In another embodiment, nucleotides can be labeled with fluorescent dyes including but not limited to fluorescein, pyrene, 7-methoxycoumarin, Cascade Blue.™., Alexa Flur 350, Alexa Flur 430, Alexa Flur 488, Alexa Flur 532, Alexa Flur 546, Alexa Flur 568, Alexa Flur 594, Alexa Flur 633, Alexa Flur 647, Alexa Flur 660, Alexa Flur 680, AMCA-X, dialkylaminocoumarin, Pacific Blue, Marina Blue, BODIPY 493/503, BODIPY FI-X, DTAF, Oregon Green 500, Dansyl-X, 6-FAM, Oregon Green 488, Oregon Green 514, Rhodamine Green-X, Rhodol Green, Calcein, Eosin, ethidium bromide, NBD, TET, 2', 4', 5', 7' tetrabromosulfone-fluorescien, BODIPY-R6G, BODIPY-FI BR2, BODIPY 530/550, HEX, BODIPY 558/568, BODIPY-TMR-X., PyMPO, BODIPY 564/570, TAMRA, BODIPY 576/589, Cy3, Rhodamine Red-x, BODIPY 581/591, carboxyXrhodamine, Texas Red-X, BODIPY-TR-X., Cy5, SpectrumAqua, SpectrumGreen #1, SpectrumGreen #2, SpectrumOrange, SpectrumRed, or naphthofluorescein.

Detection moieties may include a vast array of different types of compounds including biopolymers and synthetic polymers. Representative biological monomer units that may be used as detection moieties, either singly or in polymeric form, include peptide nucleic acids (PNAs) amino acids, non-natural amino acids, nucleic acids, saccharides, carbohydrates, peptide mimics and nucleic acid mimics. Preferred peptides are naturally occurring, stable and relatively small (e.g., the neuropeptide Substance P). Preferred amino acids also include those with simple aliphatic side chains (e.g., glycine, alanine, valine, leucine and isoleucine), amino acids with aromatic side chains (e.g., phenylalanine, tryptophan, tyrosine, and histidine), amino acids with oxygen and sulfur containing side chains (e.g., serine, threonine, methionine and cysteine), amino acids with side chains containing carboxylic or amide groups (e.g., aspartic acid, glutamic acid, asparagine and glutamine), and amino acids with side chains containing strongly basic groups (e.g., lysine and arginine), and proline. Derivatives of the above described amino acids are also contemplated as monomer units. An amino acid derivative as used herein is any compound that contains within its structure the basic amino acid core of an a amino-substituted carboxylic acid, with representative examples including but not limited to azaserine, fluoroalanine, GABA, ornithine, norleucine and cycloserine. Peptides derived from the above described amino acids can also be used as monomer units. Representative examples include both naturally occurring and synthetic peptides with molecular weight above about 500 Daltons, with peptides from about 500-5000 Daltons being preferred. Representative examples of saccharides include ribose, arabinose, xylose, glucose, galactose and other sugar derivatives composed of chains from 2-7 carbons. Representative polysaccharides include combinations of the saccharide units listed above linked via a glycosidic bond. Generally, the sequence of the polymeric units within any one detection moiety is not critical; the total mass is the key feature of the label. In an embodiment of the invention, peptide detection moieties are combined with nucleotides to yield a library of MDP's. For example, the same peptide (e.g., Substance P: an 11-amino acid polypeptide with the sequence: Arg Pro Lys Pro Gln Gln Phe Phe Gly Leu Met (SEQ ID NO: 1)) is conjugated to a library of nucleotides of differing masses (e.g., all possible 4-mers).

The monomer units according to the present invention also may be composed of nucleobase compounds or nucleoside modifications. As used herein, the term nucleobase refers to any moiety that includes within its structure a purine, a pyrimidine, a nucleic acid, nucleoside, nucleotide or derivative of any of these, such as a protected nucleobase, purine analog, pyrimidine analog, folinic acid analog, methyl phosphonate derivatives, phosphotriester derivatives, borano phosphate derivatives or phosphorothioate derivatives.

Detection moieties according to the present invention may also include any organic or inorganic polymer that has a defined mass value, remains water soluble during bioassays and is detectable by mass spectrometry. Representative synthetic monomer units that may be used as mass units in polymeric form include polyethylene glycols, polyvinyl phenols, polymethyl methacrylates, polypropylene glycol, polypyroles, and derivatives thereof. A wide variety of polymers would be readily available to one of skill in the art. The polymers may be composed of a single type of monomer unit or combinations of monomer units to create a mixed polymer. The sequence of the polymeric units within any one detection moiety is not critical; the total mass is the key feature of the label.

For nonvolatile detection moieties having mass below about 500 Da, usually significant ionic character is required; representative examples include polyethylene glycol oligomers of quaternary ammonium salts (e.g., R—(O—CH$_2$-CH$_2$)$_n$-N(CH$_3$)$_3$$^+$.Cl$^-$) and polyethylene glycol oligomers of carboxylic acids and salts (e.g., R—(O—CH$_2$-CH$_2$)$_n$-CO$_2$$^-$.Na$^+$).

Examples of involatile detection moieties typically include small oligomers of polyethylene glycol and small peptides (natural or modified) less than about 500 Da in molecular weight. In these instances, as for all of the cases considered herein, mass analysis is not by electron attachment.

Detection moieties of the present invention may also include a variety of nonvolatile and involatile organic compounds which are nonpolymeric. Representative examples of nonvolatile organic compounds include heme groups, dyes, organometallic compounds, steroids, fullerenes, retinoids, carotenoids and polyaromatic hydrocarbons.

It is preferable when using multiple detection moieties on a detector oligonucleotide, to avoid signal overlap. In addition to presenting a large, primary signal for a detection moiety with a single charge, there is also the potential for multiply charged versions of a detection moiety to present a signal as well as dimerized versions of a detection moiety. The presence of multiple signals for a single detection moiety can potentially overlap with and obscure the signal for the primary peak of a second detection moiety. Thus typically the range of detection moieties used for a given analysis may have a mass range where no multiply charged or dimer species can interfere with the detection of all detection moieties, for example, the detection moieties may have a range of masses wherein the smallest mass-label is more than half the mass of the largest detection moiety.

Other detection moieties include base-linked fluors and quenchers, which are well-known in the art. They can be obtained, for example, from Life Technologies (Gaithersburg, Md.), Sigma-Genosys (The Woodlands, Tex.), Invitrogen (Carlsbad, Calif.), or Synthetic Genetics (San Diego, Calif.). In some cases, base-linked fluors are incorporated into the oligonucleotides by post-synthesis modification of oligonucleotides that were synthesized with reactive groups linked to bases. The fluor can be attached to the 3' OH of the sugar or the base. Base-linked fluors and/or quenchers may be used to create unique MDP's of a particular mass, which can then be detected by mass spectrometry.

In another embodiment, the detector oligonucleotide comprises non-cleavable (i.e., non-degradable or nuclease-resistant) nucleotides. As described herein, an enzyme of the invention can cleave any bonds in the detector oligonucleotide that are nuclease-susceptible. However, an advantage of having at least one nuclease-resistant bond in the target-binding moiety (i.e., the portion of the detector oligonucleotide that hybridizes with or is complementary to the target nucleic acid) is that a detector oligonucleotide will yield a single-sized species of mass-distinguishable product upon cleavage. A particularly preferred non-cleavable (or cleavage resistant) nucleotide is a locked nucleic acid (LNA). Locked nucleic acid, also referred to as inaccessible RNA, is a modified RNA nucleotide. The ribose moiety of an LNA nucleotide is often modified with an extra bridge connecting the 2' and 4' carbons. LNA nucleotides can be incorporated in with DNA or RNA bases in the oligonucleotide detector whenever desired. In one embodiment, the one or more LNAs are incorporated into the 5' end of the complementary (or target-binding moiety) region of the detector oligonucleotide.

The locked ribose conformation enhances base stacking and backbone pre-organization, and thereby significantly increases the thermal stability (melting temperature) of the detector oligonucleotides where the LNA's are incorporated. This effect may be further enhanced by placing two or more LNAs adjacent to each other. See Example 3 below.

Nuclease-cleavable bonds can include, for example, a phosphodiester bond, and nuclease-resistant bonds can include, for example, thiophosphate, phosphinate, methylphosphonate, phosphoramidate, or a linker other than a phosphorous acid derivative, such as amide and boronate linkages or alkylsilyldiester and peptide nucleic acid.

In another embodiment, the detector oligonucleotide comprises groups or linkages cleavable by an enzyme. Enzymatically-cleavable release groups include phosphodiester or amide linkages as well as restriction endonuclease recognition sites.

In another embodiment, the detector oligonucleotide comprises a minor groove binder (MGB), wherein the MGB is on the 5' end, middle, or 3' end of the detector oligonucleotide—depending on the particular assay. Minor groove binding proteins and/or a modified base DNA probes with conjugated minor groove binder (MGB) groups form extremely stable duplexes with single-stranded DNA targets, allowing shorter probes to be used for hybridization based assays (e.g., U.S. Pat. No. 5,801,155). Accordingly, in some embodiments, minor groove binder groups are also included in the detector oligonucleotide, e.g., at the 3' end of the probe. A variety of suitable minor groove binders have been described in the literature. See, for example, U.S. Pat. No. 5,801,155; Wemmer & Dervan, Current Opinon in Structural Biology 7:355-361-(1997); Walker, et al., Biopolymers 44:323-334 (1997); Zimmer & Wahnert, Prog. Biophys. Molec. Bio. 47:31-112 (1986); and Reddy, et al., Pharmacol. Therap. 84:1-111 (1999). Suitable methods for attaching MGBs (as well as other moieties) through linkers to oligonucleotides are described in, for example, U.S. Pat. Nos. 5,512,677; 5,419,966; 5,696,251; 5,585,481; 5,942,610 and 5,736,626, all of which are hereby incorporated by reference.

In another embodiment, the detector oligonucleotide comprises isotopically-coded nucleotides. In one example, an allele-specific detector oligonucleotide comprises an isotopically-coded nucleotide that hybridizes to the SNP allele. The isotopically-coded detector oligonucleotide in turn yields an isotopically-coded mass-distinguishable product. In one embodiment, only single isotopically-coded nucleotides or short fragments comprising isotopically-coded nucleotides (e.g., two, three or four bases) are generated and detected by mass spectrometry. When only single nucleotides are detected, purification is simplified since phosphate backbones are not present and salt adduct formation is minimized. See, for example U.S. Pat. No. 6,613,509 (hereby incorporated by reference), which describes incorporation of isotopes into nucleic acids.

In another embodiment, the detector oligonucleotide may be modified to increase its melting temperature (Tm). In one embodiment, the primer melting temperature often is around 58-60° C., and detector oligonucleotide Tm often is 10° C. higher than the primer's Tm. The Tm of both the primers often is approximately equal.

G. DETECTOR OLIGONUCLEOTIDE BINDING PROPERTIES

In some embodiments, degradation of the detector oligonucleotide is performed under conditions wherein one or more of the nucleic acids in the structure can disassociate from the target. In one embodiment, full or partial disassociation of the detector oligonucleotide allows the formation of multiple mass-distinguishable products. In some embodiments, said disassociation is induced by an increase in temperature, such that one or more oligonucleotides can no longer hybridize to the target strand. In other embodiments, said disassociation occurs because cleavage of an oligonucleotide produces only cleavage products that cannot bind to the target strand under the conditions of the reaction. In a preferred embodiment, conditions are selected wherein an oligonucleotide may associate with (i.e., hybridize to) and disassociate from a target strand regardless of cleavage. In a particularly preferred embodiment, conditions are selected such that the number of copies of the detector oligonucleotide that can be cleaved when part of a duplex structure exceeds the number of copies of the target nucleic acid strand by a sufficient amount that when the partially cleaved detector oligonucleotide disassociates, the probability that the target strand will associate with an intact copy of the detector oligonucleotide is greater than the probability that it will associate with a cleaved copy of the detector oligonucleotide.

H. MASS-DISTINGUISHABLE PRODUCT DETECTION METHODS

Mass-distinguishable products are distinguished by a particular physical attribute or detection feature, including but not limited to length, mass, charge, or charge-to-mass ratio. In a preferred embodiment, the detection feature is mass. In another related embodiment, the MDP may be distinguished by a behavior that is related to a physical attribute, including but not limited to mass, time of flight in MALDI-TOF mass spectrometry. In a related embodiment, MDP's from one or more detector oligonucleotides are released and selectively desorbed from a mass spectral matrix such that the non-selective primers and detector oligonucleotides (i.e., the target nucleic acid is not present) do not desorb. For these embodiments, the MDP's should desorb more efficiently from the mass spectral matrix than detector oligonucleotides or other non-MDP's present in the reaction mixture. Preferred mass spectral matrices include 2,5-dihydroxybenzoic acid, alpha-cyano-4-hydroxycinammic acid, 3-hydroxypicolinic acid (3-HPA), di-ammoniumcitrate (DAC) and combinations thereof. In another embodiment, the mass spectral matrices may be designed for the analysis of proteins. Exemplary matrices for protein analysis include, but are not limited to, DHB and CHCA.

The method can further include an additional step of separating one or more detector oligonucleotide fragments (i.e., MDP's) from un-cleaved or partially-cleaved detector oligonucleotides. Separation can be accomplished using capture ligands, such as biotin or other affinity ligands, and capture agents, such as avidin, streptavidin, an antibody, a receptor, a capture probe that is complementary to the MDP, or a functional fragment thereof, having specific binding activity to the capture ligand. A MDP can contain a capture ligand having specific binding activity for a capture agent. For example, the MDP can be biotinylated or attached to an affinity ligand using methods well known in the art. See Example 4 below. A capture ligand and capture agent can also be used to add mass to the remaining part of the MDP such that it can be excluded from the mass range of the MDP detected in a mass spectrometer. In one embodiment, the capture probe may have a universal primer for universal amplification of cleavage product.

A separation step can also be used to remove salts, enzymes, or other buffer components from the MDP's. Several methods well known in the art, such as chromatography, gel electrophoresis, or precipitation, can be used to clean up the sample. For example, size exclusion chromatography or affinity chromatography can be used to remove salt from a sample. The choice of separation method can depend on the amount of a sample. For example, when small amounts of sample are available or a miniaturized apparatus is used, a micro-affinity chromatography separation step can be used. In addition, whether a separation step is desired, and the choice of separation method, can depend on the detection method used. For example, the efficiency of matrix-assisted laser desorption/ionization and electrospray ionization can be improved by removing salts from a sample. For example, salts can absorb energy from the laser in matrix-assisted laser desorption/ionization and result in lower ionization efficiency.

Mass spectrometry is the preferred method to detect mass-distinguishable products of the invention and thus identify and/or quantitate target nucleic acids. Mass-distinguishable products can be ionized in a mass spectrometer and the ions separated in space or time based on their mass-to-charge ratio. The mass spectrometer then calculates a mass associated with each ion. Therefore, when referring to mass spectrometry, the term mass can be used for simplicity to describe a mass-to-charge ratio.

Mass spectrometry is a sensitive and accurate technique for separating and identifying molecules. Generally, mass spectrometers have two main components, an ion source for the production of ions and a mass-selective analyzer for measuring the mass-to-charge ratio of ions, which is and converted into a measurement of mass for these ions. Several ionization methods are known in the art and described herein. A mass-distinguishable product can be charged prior to, during or after cleavage from the detector oligonucleotide. Consequently, a mass-distinguishable product that will be measured by mass spectrometry does not always require a charge since a charge can be acquired through the mass spectrometry procedure. In mass spectrometry analysis, optional components of a MDP such as charge and detection moieties can be used to contribute mass to the MDP.

Different mass spectrometry methods, for example, quadrupole mass spectrometry, ion trap mass spectrometry, time-of-flight mass spectrometry, gas chromatography mass spectrometry and tandem mass spectrometry, as described herein, can utilize various combinations of ion sources and mass analyzers which allows for flexibility in designing customized detection protocols. In addition, mass spectrometers can be programmed to transmit all ions from the ion source into the mass spectrometer either sequentially or at the same time. Furthermore, a mass spectrometer can be programmed to select ions of a particular mass for transmission into the mass spectrometer while blocking other ions.

The ability to precisely control the movement of ions in a mass spectrometer allows for greater options in detection protocols which can be advantageous when a large number of mass-distinguishable products, for example, from a multiplex experiment, are being analyzed. For example, in a multiplex experiment with a large number of MDP's it can be advantageous to select individual reporters from a group of similar reporters and then analyze that reporter separately. Another advantage based on controlling the mass range detected by the mass spectrometer includes the ability to exclude un-cleaved or partially-cleaved tagged probes from being analyzed which reduces background noise from the assay.

Mass spectrometers can resolve ions with small mass differences and measure the mass of ions with a high degree of accuracy. Therefore, MDP's of similar masses can be used together in the same experiment since the mass spectrometer can differentiate the mass of even closely related tags. The high degree of resolution and mass accuracy achieved using mass spectrometry methods allows the use of large sets of tagged probes because the resulting reporter tags can be distinguished from each other. The ability to use large sets of tagged probes is an advantage when designing multiplex experiments.

Another advantage of using mass spectrometry for detecting the mass of a mass-distinguishable product is based on the high sensitivity of this type of mass analysis. Mass spectrometers achieve high sensitivity by utilizing a large portion of the ions that are formed by the ion source and efficiently transmitting these ions through the mass analyzer to the detector. Because of this high level of sensitivity, even limited amounts of sample can be measured using mass spectrometry. This can be an advantage in a multiplex experiment where the amount of each MDP species may be small.

Mass spectrometry methods are well known in the art (see Burlingame et al. Anal. Chem. 70:647R-716R (1998); Kinter and Sherman, Protein Sequencing and Identification Using Tandem Mass Spectrometry Wiley-Interscience, New York (2000)). The basic processes associated with a mass spectrometry method are the generation of gas-phase ions derived from the sample, and the measurement of their mass.

The movement of gas-phase ions can be precisely controlled using electromagnetic fields generated in the mass spectrometer. The movement of ions in these electromagnetic fields is proportional to the m/z of the ion and this forms the basis of measuring the m/z and therefore the mass of a sample. The movement of ions in these electromagnetic fields allows the ions to be contained and focused which accounts for the high sensitivity of mass spectrometry. During the course of m/z measurement, ions are transmitted with high efficiency to particle detectors that record the arrival of these ions. The quantity of ions at each m/z is demonstrated by peaks on a graph where the x axis is m/z and the y axis is relative abundance. Different mass spectrometers have different levels of resolution, that is, the ability to resolve peaks between ions closely related in mass. The resolution is defined as R=m/delta m, where m is the ion mass and delta m is the difference in mass between two peaks in a mass spectrum. For example, a mass spectrometer with a resolution of 1000 can resolve an ion with a m/z of 100.0 from an ion with a m/z of 100.1.

Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Exemplary mass analyzers include a quadrupole mass filter, ion trap mass analyzer and time-of-flight mass analyzer.

The ion formation process is a starting point for mass spectrum analysis. Several ionization methods are available and the choice of ionization method depends on the sample to be analyzed. For example, for the analysis of polypeptides a relatively gentle ionization procedure such as electrospray ionization (ESI) can be desirable. For ESI, a solution containing the sample is passed through a fine needle at high potential which creates a strong electrical field resulting in a fine spray of highly charged droplets that is directed into the mass spectrometer. Other ionization procedures include, for example, fast-atom bombardment (FAB) which uses a high-energy beam of neutral atoms to strike a solid sample causing desorption and ionization. Matrix-assisted laser desorption ionization (MALDI) is a method in which a laser pulse is used to strike a sample that has been crystallized in an UV-absorbing compound matrix. Other ionization procedures known in the art include, for example, plasma and glow discharge, plasma desorption ionization, resonance ionization, and secondary ionization. A mass-distinguishable product can become ionized prior to, during, or after cleavage from the tagged probe.

Electrospray ionization (ESI) has several properties that are useful for the invention described herein. For example, ESI can be used for biological molecules such as polypeptides that are difficult to ionize or vaporize. In addition, the efficiency of ESI can be very high which provides the basis for highly sensitive measurements. Furthermore, ESI produces charged molecules from solution, which is convenient for analyzing mass-distinguishable products that are in solution. In contrast, ionization procedures such as MALDI require crystallization of the sample prior to ionization.

Since ESI can produce charged molecules directly from solution, it is compatible with samples from liquid chromatography systems. For example, a mass spectrometer can have an inlet for a liquid chromatography system, such as an HPLC, so that fractions flow from the chromatography column into the mass spectrometer. This in-line arrangement of a liquid chromatography system and mass spectrometer is sometimes referred to as LC-MS. A LC-MS system can be used, for example, to separate un-cleaved or partially cleaved MDP's from cleaved MDP's before mass spectrometry analysis. In addition, chromatography can be used to remove salts or other buffer components from the MDP sample before mass spectrometry analysis. For example, desalting of a sample using a reversed-phase HPLC column, in-line or off-line, can be used to increase the efficiency of the ionization process and thus improve sensitivity of detection by mass spectrometry.

A variety of mass analyzers are available that can be paired with different ion sources. Different mass analyzers have different advantages as known to one skilled in the art and as described herein. The mass spectrometer and methods chosen for detection depends on the particular assay, for example, a more sensitive mass analyzer can be used when a small amount of ions are generated for detection. Several types of mass analyzers and mass spectrometry methods are described below.

Ion mobility mass (IM) spectrometry is a gas-phase separation method that adds new dimensions to mass spectrometry (MS). IM separates gas-phase ions based on their collision cross-section and can be coupled with time-of-flight (TOF) mass spectrometry to yield a powerful tool used in the identification and characterization of proteins and peptides. Therefore, IM-MS has particular utility for the present invention when the mass-distinguishable product is a protein or peptide. IM-MS is discussed in more detail by Verbeck et al. in the *Journal of Biomolecular Techniques* (Vol 13, Issue 2, 56-61).

Quadrupole mass spectrometry utilizes a quadrupole mass filter or analyzer. This type of mass analyzer is composed of four rods arranged as two sets of two electrically connected rods. A combination of rf and dc voltages are applied to each pair of rods which produces fields that cause an oscillating movement of the ions as they move from the beginning of the mass filter to the end. The result of these fields is the production of a high-pass mass filter in one pair of rods and a low-pass filter in the other pair of rods. Overlap between the high-pass and low-pass filter leaves a defined m/z that can pass both filters and traverse the length of the quadrupole. This m/z is selected and remains stable in the quadrupole mass filter while all other m/z have unstable trajectories and do not remain in the mass filter. A mass spectrum results by ramping the applied fields such that an increasing m/z is selected to pass through the mass filter and reach the detector. In addition, quadrupoles can also be set up to contain and transmit ions of all m/z by applying a rf-only field. This allows quadrupoles to function as a lens or focusing system in regions of the mass spectrometer where ion transmission is needed without mass filtering. This will be of use in tandem mass spectrometry as described further below.

A quadrupole mass analyzer, as well as the other mass analyzers described herein, can be programmed to analyze a defined m/z or mass range. This property of mass spectrometers is useful for the invention described herein. Since the mass range of cleaved mass-distinguishable products will be known prior to an assay, a mass spectrometer can be programmed to transmit ions of the projected correct mass range while excluding ions of a higher or lower mass range. The ability to select a mass range can decrease the background noise in the assay and thus increase the signal-to-noise ratio. In addition, a defined mass range can be used to exclude analysis of any un-cleaved detector oligonucleotides, which would be of higher mass than the mass of the mass-distinguishable products. Therefore, the mass spectrometer can accomplish an inherent separation step as well as detection and identification of the mass-distinguishable products.

Ion trap mass spectrometry utilizes an ion trap mass analyzer. In these mass analyzers, fields are applied so that ions of all m/z are initially trapped and oscillate in the mass analyzer. Ions enter the ion trap from the ion source through a focusing device such as an octapole lens system. Ion trapping takes place in the trapping region before excitation and ejection through an electrode to the detector. Mass analysis is accomplished by sequentially applying voltages that increase the amplitude of the oscillations in a way that ejects ions of increasing m/z out of the trap and into the detector. In contrast to quadrupole mass spectrometry, all ions are retained in the fields of the mass analyzer except those with the selected m/z. One advantage to ion traps is that they have very high sensitivity, as long as one is careful to limit the number of ions being tapped at one time. Control of the number of ions can be accomplished by varying the time over which ions are injected into the trap. The mass resolution of ion traps is similar to that of quadrupole mass filters, although ion traps do have low m/z limitations.

Time-of-flight mass spectrometry utilizes a time-of-flight mass analyzer. For this method of m/z analysis, an ion is first given a fixed amount of kinetic energy by acceleration in an electric field (generated by high voltage). Following acceleration, the ion enters a field-free or "drift" region where it travels at a velocity that is inversely proportional to its m/z. Therefore, ions with low m/z travel more rapidly than ions with high m/z. The time required for ions to travel the length of the field-free region is measured and used to calculate the m/z of the ion.

One consideration in this type of mass analysis is that the set of ions being studied be introduced into the analyzer at the same time. For example, this type of mass analysis is well suited to ionization techniques like MALDI which produces ions in short well-defined pulses. Another consideration is to control velocity spread produced by ions that have variations in their amounts of kinetic energy. The use of longer flight tubes, ion reflectors, or higher accelerating voltages can help minimize the effects of velocity spread. Time-of-flight mass analyzers have a high level of sensitivity and a wider m/z range than quadrupole or ion trap mass analyzers. Also data can be acquired quickly with this type of mass analyzer because no scanning of the mass analyzer is necessary.

Gas chromatography mass spectrometry offers a nice solution for detecting a target in real-time. The gas chromatography (GC) portion of the system separates the chemical mixture into pulses of analyte (e.g., MDP's) and the mass spectrometer (MS) identifies and quantifies the analyte.

Tandem mass spectrometry can utilize combinations of the mass analyzers described above. Tandem mass spectrometers can use a first mass analyzer to separate ions according to their m/z in order to isolate an ion of interest for further analysis. The isolated ion of interest is then broken into fragment ions (called collisionally activated dissociation or collisionally induced dissociation) and the fragment ions are analyzed by the second mass analyzer. These types of tandem mass spectrometer systems are called tandem in space systems because the two mass analyzers are separated in space, usually by a collision cell. Tandem mass spectrometer systems also include tandem in time systems where one mass analyzer is used, however the mass analyzer is used sequentially to isolate an ion, induce fragmentation, and then perform mass analysis.

Mass spectrometers in the tandem in space category have more than one mass analyzer. For example, a tandem quadrupole mass spectrometer system can have a first quadrupole mass filter, followed by a collision cell, followed by a second quadrupole mass filter and then the detector. Another arrangement is to use a quadrupole mass filter for the first mass analyzer and a time-of-flight mass analyzer for the second mass analyzer with a collision cell separating the two mass analyzers. Other tandem systems are known in the art including reflectron-time-of-flight, tandem sector and sector-quadrupole mass spectrometry.

Mass spectrometers in the tandem in time category have one mass analyzer that performs different functions at different times. For example, an ion trap mass spectrometer can be used to trap ions of all m/z. A series of rf scan functions are applied which ejects ions of all m/z from the trap except the m/z of ions of interest. After the m/z of interest has been isolated, an rf pulse is applied to produce collisions with gas molecules in the trap to induce fragmentation of the ions. Then the m/z values of the fragmented ions are measured by the mass analyzer. Ion cyclotron resonance instruments, also known as Fourier transform mass spectrometers, are an example of tandem-in-time systems.

Several types of tandem mass spectrometry experiments can be performed by controlling the ions that are selected in each stage of the experiment. The different types of experiments utilize different modes of operation, sometimes called "scans," of the mass analyzers. In a first example, called a mass spectrum scan, the first mass analyzer and the collision cell transmit all ions for mass analysis into the second mass analyzer. In a second example, called a product ion scan, the ions of interest are mass-selected in the first mass analyzer and then fragmented in the collision cell. The ions formed are then mass analyzed by scanning the second mass analyzer. In a third example, called a precursor ion scan, the first mass analyzer is scanned to sequentially transmit the mass analyzed ions into the collision cell for fragmentation. The second mass analyzer mass-selects the product ion of interest for transmission to the detector. Therefore, the detector signal is the result of all precursor ions that can be fragmented into a common product ion. Other experimental formats include neutral loss scans where a constant mass difference is accounted for in the mass scans. The use of these different tandem mass spectrometry scan procedures can be advantageous when large sets of reporter tags are measured in a single experiment as with multiplex experiments.

In typical applications, the amount of mass-distinguishable product generated by the during the reaction is determined based on cycle threshold (Ct) value, which represents the number of cycles required to generate a detectable amount of nucleic acid. Determination of Ct values is well known in the art. Briefly, during PCR, as the amount of formed amplicon increases, the signal intensity increases to a measurable level and reaches a plateau in later cycles when the reaction enters into a non-logarithmic phase. By plotting signal intensity versus the cycle number during the logarithmic phase of the reaction, the specific cycle at which a measurable signal is obtained can be deduced and used to calculate the quantity of the target before the start of the PCR. Exemplary methods of determining Ct are described in, e.g., Heid et al. *Genome Methods* 6:986-94, 1996, with reference to hydrolysis probes.

For quantification, one may choose to use controls, which provide a signal in relation to the amount of the target that is present or is introduced. A control to allow conversion of relative mass signals into absolute quantities is accomplished by addition of a known quantity of a mass tag or mass label to each sample before detection of the mass-distinguishable products. See for example, Ding and Cantor Proc Natl Acad Sci USA. 2003 Mar. 18; 100(6):3059-64, who describe a method for quantitative gene expression analysis, wherein the control nucleotide contains an artificial single nucleotide polymorphism to distinguish it from the gene of interest. Any mass tag that does not interfere with detection of the MDP's can be used for normalizing the mass signal. Such standards preferably have separation properties that are different from those of any of the molecular tags in the sample, and could have the same or a different mass signatures.

I. COMPOSITIONS AND KITS

In another aspect, the present invention includes kits for performing the methods of the invention, such kits comprising a primers (e.g., universal primers) and detector oligonucleotides for detecting or measuring one or more target nucleic acids. Such kits further comprising an enzyme and appropriate buffers for performing amplification reactions that cleave and release detector oligonucleotides or fragments thereof for detection. In certain embodiments, a kit may include one or more detector oligonucleotides that can result in one or more mass-distinguishable products, and one or more reagents associated with mass spectrometry, the latter of which may be, for example, one or more mass standards (e.g., for use as an internal standard), a matrix for matrix-assisted laser desorption ionization (MALDI) mass spectrometry (e.g., 3-hydroxypicolinic acid), a nucleic acid binding resin (e.g., $C^{18}$ resin), and/or a solution for conditioning a nucleic acid (e.g., a salt solution).

EXAMPLES

The examples provided hereafter illustrate and do not limit the invention.

Example 1

Detection of Exon 10 of the RhD Gene

Figure 8:
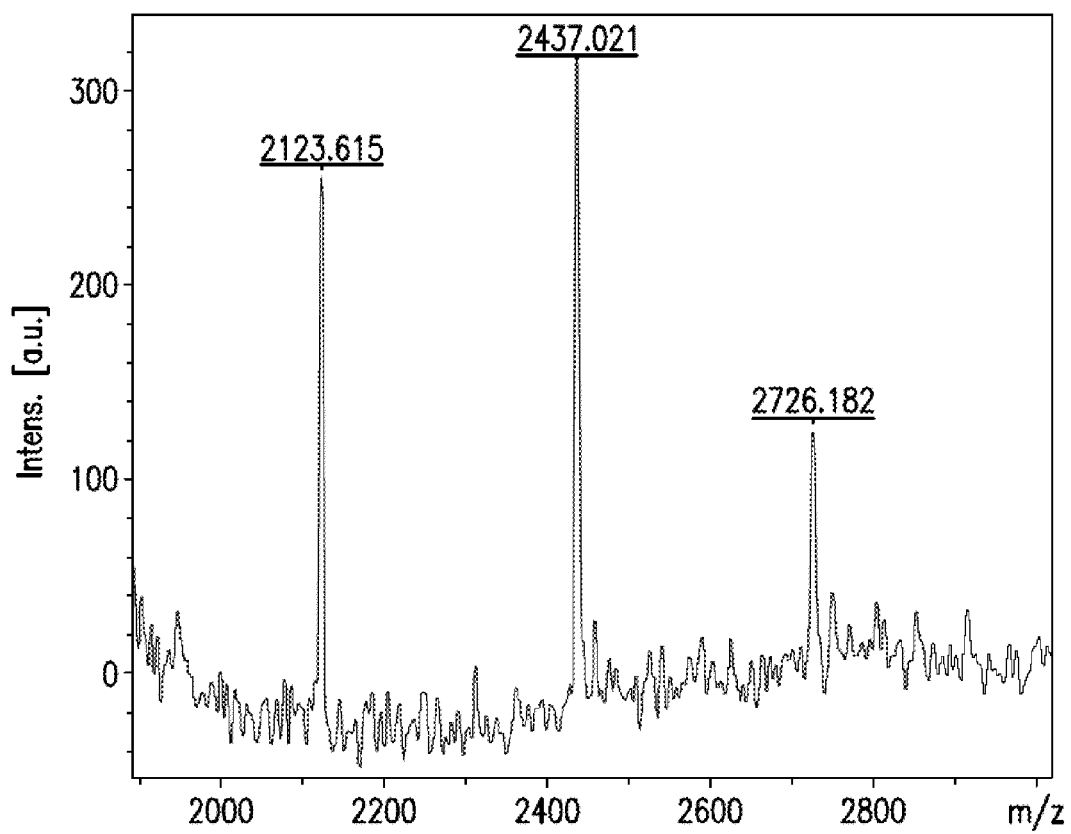
FIG. 8 is a mass spectrogram showing the MDP's generated from the Exon10 specific detector oligonucleotide during PCR amplification (mass range between 1900 and 3000 Da). The mass signals at 2123.6 Da, 2437.0 Da and 2726.2 Da represent 5' MDP's containing the polyA tag (6 Adenine) cleaved at the first hybridized T nucleotide (AAAAAAT), the polyA tag cleaved after the first two hybridized nucleotides (AAAAAATA) and after the first three hybridized nucleotides (AAAAAATAC). The Y-axis is signal intensity and the X-axis is mass to charge ratio.

A detection assay was performed to detect the exon10 region of the Rhesus D gene. Design of PCR primers and detector oligonucleotide was performed according to the detailed description section. In this particular assay, the detector oligonucleotide carries a non-complementary 5' overhang consisting of 6 Adenines. Since the target sequence (Exon10 of RhD) was present in the sample, the PCR primers and the detector oligonucleotide hybridized to the target. During amplification, the detector oligonucleotide was degraded by the 5' nuclease activity of the DNA polymerase extending from the upstream PCR primer. During degradation, mass-distinguishable products (MDP's) including the 5' polyA tag were released and identified unambiguously by mass spectrometric analysis (See FIG. 8). Detection of these mass signals confirmed the presence of the target nucleic acid.

Primer and Detector Oligonucleotide Sequences:

The following primers were used for amplification of a partial sequence within Exon 10 of the Rhesus D (RhD) gene:

```
                                        (SEQ ID NO: 2)
Forward PCR primer:    5' CCTCTCACTGTTGCCTGCATT 3'

(SEQ ID NO: 3)
Reverse PCR primer:    5' AGTGCCTGCGCGAACATT 3'
```

The following detector oligonucleotide hybridized to the target and was degraded to yield MDP's that were detected by mass spectrometry:

```
    Detector oligonucleotide:
                                        (SEQ ID NO: 4)
    5' AAAAAAATTGCTGTCTGATCTTTATCCTCCGTTCCCT 3'
```

PCR Mix:

PCR primers were used at a final concentration of 900 nM for the PCR primers and at 200 nM of the detector oligonucleotide.

The PCR mix also contained 20 ng of genomic DNA (of an RhD+ individual), 25 ul of 2× PCR Mastermix (ABI Taq-Man® PCR master mix including buffer and AmpliTaq® Gold enzyme) and water to a final volume of 50 ul.

Reactions were performed in a 96-well ABGene microtiter plate.

Cycling Conditions:

The PCR mix was activated for 10 minutes at 95° C. and then subjected to 40 cycles of 95° C. for 15 seconds and 60° C. for 1 minute.

Sample Preparation for Mass Spectrometric Analysis:

10 ul of PCR product were transferred to a new 96-well microtiter plate and 20 ul of water containing 15 mg of ammonium-loaded ion-exchange resin (Clean Resin, SEQUENOM®) were added to the PCR product. The reaction mix was incubated for 15 minutes and gentle rotation.

A pintool device (Nanodispenser, SEQUENOM®) was used to transfer 15 nl of analyte on a miniaturized chip array (SpectroCHIP®, SEQUENOM®).

Mass Spectral Analysis:

Data acquisition and analysis were performed using a bench-top, linear MALDI-TOF mass spectrometer (Compact Analyzer, SEQUENOM®). For each spectrum at least 20 laser shots were accumulated. Presence of the target nucleic acid (here Exon 10 of the RhD gene) was identified by the mass-distinguishable products (MDP's) of the Exon10 specific detector oligonucleotide. The MALDI-TOF MS spectrum exemplifies detection of exon10 of the RhD gene (see FIG. 8). The three MDP's can only be generated when the target sequence (Exon10 of the RhD gene) is present during amplification and when the detector oligonucleotide can hybridize to the target nucleic acid during amplification.

Example 2

Detection of Exon 5 of the RhD Gene

Figure 9:
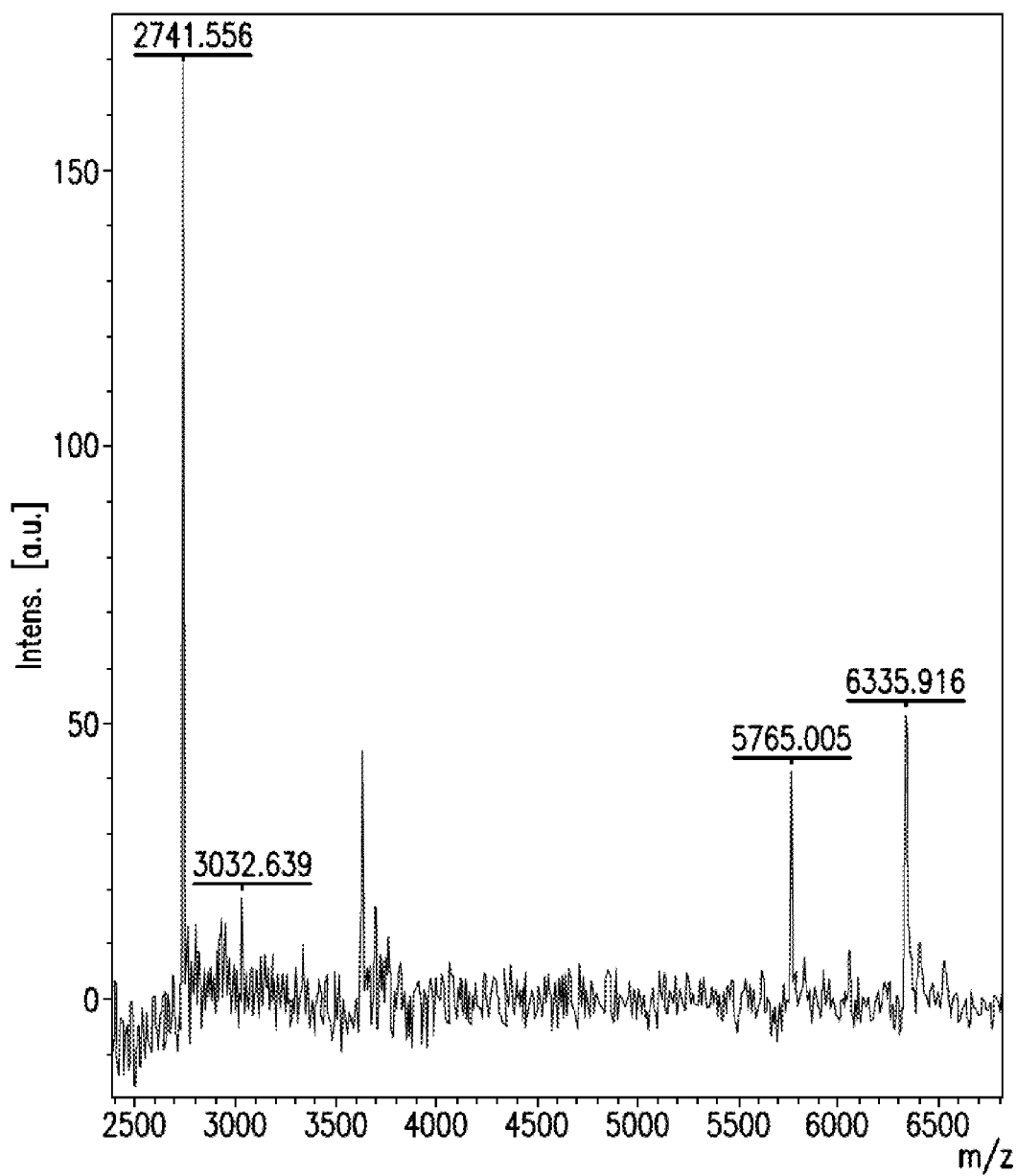
FIG. 9 provides an experimental spectrogram where a 5' non-complementary MDP is generated and detected. The term "identifies target NS" at the bottom of the Figure refers to "identifies target nucleotide sequence."

A detection assay was performed to detect the exon5 region of the Rhesus D gene. Design of PCR primers and detector oligonucleotide was performed according to the detailed description section. In this particular assay, the detector oligonucleotide carries a non-complementary 5' overhang consisting of 8 Adenines. Since the target sequence (Exon5 of RhD) was present in the sample, the PCR primers and the detector oligonucleotide hybridized to the target. During amplification, the detector oligonucleotide was degraded by the 5' nuclease activity of the DNA polymerase extending from the upstream PCR primer. During degradation, mass-distinguishable products (MDP's) including the 5' polyA tag were released and identified unambiguously by mass spectrometric analysis (See FIG. 9). Detection of these mass signals confirmed the presence of the target nucleic acid.

Primer and Detector Oligonucleotide Sequences:

The following primers were used for amplification of a partial sequence within Exon 5 of the Rhesus D (RhD) gene:

```
                                        (SEQ ID NO: 5)
Forward PCR primer:    5' CGCCCTCTTCTTGTGGATG 3'

(SEQ ID NO: 6)
Reverse PCR primer:    5' GAACACGGCATTCTTCCTTTC 3'
```

The following detector oligonucleotide hybridized to the target and was degraded to yield MDP's that were detected by mass spectrometry:

```
    Detector oligonucleotide:
                                        (SEQ ID NO: 7)
    5' AAAAAAAATCTGGCCAAGTTTCAACTCTGCTCGCT 3'
```

PCR Mix:

PCR primers were used at a final concentration of 900 nM for the PCR primers and at 200 nM of the detector oligonucleotide.

The PCR mix also contained 20 ng of genomic DNA (of an RhD+ individual), 25 ul of 2×PCR Mastermix (ABI TaqMan PCR master mix including buffer and AmpliTaq Gold enzyme) and water to a final volume of 50 ul.

Reactions were performed in a 96-well ABGene microtiter plate.

Cycling Conditions:

The PCR mix was activated for 10 minutes at 95° C. and then subjected to 40 cycles of 95° C. for 15 seconds and 60° C. for 1 minute.

Sample Preparation for Mass Spectrometric Analysis:

10 ul of PCR product were transferred to a new 96-well microtiter plate and 20 ul of water containing 15 mg of ammonium-loaded ion-exchange resin (Clean Resin, SEQUENOM, Inc®) were added to the PCR product. The reaction mix was incubated for 15 minutes and gentle rotation.

A pintool device (Nanodispenser, SEQUENOM, Inc®) was used to transfer 15 nl of analyte on a miniaturized chip array (SpectroCHIP™, SEQUENOM, Inc®).

Mass Spectral Analysis:

Data acquisition and analysis were performed using a bench-top, linear MALDI-TOF mass spectrometer (Compact Analyzer, SEQUENOM, Inc®). For each spectrum at least 20 laser shots were accumulated. Presence of the target nucleic acid (here Exon 5 of the RhD gene) was identified by the mass-distinguishable products (MDP's) of the Exon5 specific detector oligonucleotide. The MALDI-TOF MS spectrum exemplifies detection of exon5 of the RhD gene (see FIG. 9). The three MDP's can only be generated when the target sequence (Exon5 of the RhD gene) is present during amplification and when the detector oligonucleotide can hybridize to the target nucleic acid during amplification.

Example 3

10-Plex Set of Y-Chromosome Markers for Gender Determination Using Modified Detector Oligonucleotides that Contain LNAs and 3' Extension Blockers A detection assay was performed to detect ten regions specific for the Y-chromosome. PCR primers and detector oligonucleotides were designed to meet the criteria described in the present invention using methods well known in the art. For example, the detector oligonucleotides were designed with a melting temperature approximately 10 degrees Celsius higher than the PCR primers. Further, a polyA/G tail was added to the 5'-end of the detector oligonucleotide with the length and sequence variable in order to space and resolve cleavage products within a 2000-6000 Da window on the MALDI-TOF MS.

In this particular multiplexed assay, the detector oligonucleotides carry a non-complementary 5'-overhang consisting of multiple Adenines and/or Guanines. In samples where the Y-chromosome is present (such as male samples), the PCR primers and the detector oligonucleotides hybridize to the target. During amplification, the detector oligonucleotides were degraded by the 5'-nuclease activity of the DNA polymerase extending from the upstream PCR primer. During degradation, nine of the ten assays were successful and mass-distinguishable products (MDP's) including the 5'-polyA or polyA/G tags were released and identified unambiguously by MALDI-TOF mass spectrometric analysis. Detection of these mass signals confirmed the presence of the target nucleic acid.

In samples where Y chromosome template is not present (such as female samples or negative control (NTC) samples), the PCR primers and the detector oligonucleotides did not hybridize to the target, and 5'-polyA or polyA/G tags were not detected.

Primer and Detector Oligonucleotide Sequences:

The detector oligonucleotides provided below hybridized to the target and were degraded to yield MDP's that were detected by mass spectrometry. The sequences may contain a "+", which represents a locked nucleic acid (LNA), or "/3Phos/" and "/InvdT/" which represent the introduction of a phosphate group and inverted deoxythymine, respectively.

Locked nucleic acids (LNAs) bind very stably with their complement and have a highly reduced rate of cleavage relative to a nascent deoxynucleotide. This serves to control the point of cleavage, and thereby produce uniform cleavage products. This effect may be further enhanced by placing two LNAs adjacent to each other.

The introduction of one or more phosphate groups or inverted deoxythymines serves to block the 3'-end of the complementary portion of the detector oligonucleotide, which prevents extension of the detector oligonucleotide by the DNA polymerase during cycling. Such unwanted extension can have several possible negative effects including competitive binding for target after 5'-tail cleavage has occurred and depletion of PCR reaction components such as dNTPs.

The following primers were used for amplification of a partial sequence within BPY2 gene (BPY2-2 assay):

Forward PCR primer:
(SEQ ID NO: 8)
5'-ACGTTGGATGATATTCTAGACTCTTCCAAGCC-3'

Reverse PCR primer:
(SEQ ID NO: 8)
5'-ACGTTGGATGAAAAAGAGGAGTGTCACTCTAC-3'

Detector oligonucleotides (multiple detector oligonucleotides were tested individually in different assays):

(SEQ ID NO: 10)
5'-AAAAAAAAAAAAAT+T+TGCAAAGCCCAGCACTGA-3'
Where + represents a locked nucleic acid (LNA)
or (SEQ ID NO: 10)
5'-AAAAAAAAAAAAAT+T+TGCAAAGCCCAGCACTGA/3Phos/-3'
or (SEQ ID NO: 10)
5'-AAAAAAAAAAAAAT+T+TGCAAAGCCCAGCACTGA/3InvdT/-3'

The following primers were used for amplification of a secondary partial sequence within CDY1 gene (CDY1-1 assay):

Forward PCR primer:
(SEQ ID NO: 11)
5'-ACGTTGGATGATGTTAGCCAGGATTGTCTCG-3'

Reverse PCR primer:
(SEQ ID NO: 12)
5'-ACGTTGGATGACACCTGTAATCCCAGCATTTT-3'

Detector Oligonucleotides:

(SEQ ID NO: 13)
5'-AAAAAAAAAG+C+TGAGGTGCTTGGATCACGA-3'
or (SEQ ID NO: 13)
5'-AAAAAAAAAG+C+TGAGGTGCTTGGATCACGA/3Phos/-3'
or (SEQ ID NO: 13)
5'-AAAAAAAAAG+C+TGAGGTGCTTGGATCACGA/3InvdT/-3'

The following primers were used for amplification of a partial sequence within CDY1 gene (CDY1-2 assay):

Forward PCR primer:
(SEQ ID NO: 14)
5'-ACGTTGGATGCAATCCCGTGTCTTTCCT-3'

Reverse PCR primer:
(SEQ ID NO: 15)
5'-ACGTTGGATGGAACCAAATACTGTGTATTCCC-3'

Detector Oligonucleotides:

(SEQ ID NO: 16)
5'-AAAAAAAAA+T+GGCTTCCCAGGAGTTTGAGG-3'
or (SEQ ID NO: 16)
5'-AAAAAAAAA+T+GGCTTCCCAGGAGTTTGAGG/3Phos/-3'
or (SEQ ID NO: 16)
5'-AAAAAAAAA+T+GGCTTCCCAGGAGTTTGAGG/3InvdT/-3'

The following primers were used for amplification of a partial sequence within CYORF14 region of the Y chromosome (CYORF14-3 assay):

Forward PCR primer:
(SEQ ID NO: 17)
5'-ACGTTGGATGTTTACATCAACAAACAAGGG-3'

Reverse PCR primer:
(SEQ ID NO: 18)
5'-ACGTTGGATGCTACTGGGTCTAGCCTTATAAT-3'

Detector Oligonucleotides:

(SEQ ID NO: 19)
5'-AAAAGGAAAAAA+G+AGGTTGACATGAAGTCATTTGCT-3'
or (SEQ ID NO: 19)
5'-AAAAGGAAAAAA+G+AGGTTGACATGAAGTCATTTGCT/
3Phos/-3'
or (SEQ ID NO: 19)
5'-AAAAGGAAAAAA+G+AGGTTGACATGAAGTCATTTGCT/
3InvdT//-3'

The following primers were used for amplification of a partial sequence within PRY gene (PRY-2 assay):

Forward PCR primer:
(SEQ ID NO: 20)
5'-ACGTTGGATGTCACTGGGATCAGGACAGAC-3'

Reverse PCR primer:
(SEQ ID NO: 21)
5'-ACGTTGGATGAGAGGAAACTGCTTCCCAAAC-3'

Detector Oligonucleotides:

(SEQ ID NO: 22)
5'-AAAAAAAAAAAAAAA+A+GCTGCCAGCAAGGAGCCT-3'
or (SEQ ID NO: 22)
5'-AAAAAAAAAAAAAAA+A+GCTGCCAGCAAGGAGCCT/3Phos/-3'
or (SEQ ID NO: 22)
5'-AAAAAAAAAAAAAAA+A+GCTGCCAGCAAGGAGCCT/3InvdT/-3'

The following primers were used for amplification of a partial sequence within RBMY1A1 gene (RBMY1A1-1 assay):

Forward PCR primer:
(SEQ ID NO: 23)
5'-ACGTTGGATGGATGGGTTTTCTATGTGTGGG-3'

Reverse PCR primer:
(SEQ ID NO: 24)
5'-ACGTTGGATGTGAGTCTCTTAATAGCACTGAG-3'

Detector Oligonucleotides:

(SEQ ID NO: 25)
5'-AAAAAAAAAA+C+GGGAGGAGTCAGTGGGGA-3'
or (SEQ ID NO: 25)
5'-AAAAAAAAAA+C+GGGAGGAGTCAGTGGGGA/3Phos/-3'
or (SEQ ID NO: 25)
5'-AAAAAAAAAA+C+GGGAGGAGTCAGTGGGGA/3InvdT/-3'

The following primers were used for amplification of a secondary partial sequence within RBMY1A1 gene (RBMY1A1-2 assay):

Forward PCR primer:
(SEQ ID NO: 26)
5'-ACGTTGGATGAGCTAATTACTCATTTCCCCAG-3'

Reverse PCR primer:
(SEQ ID NO: 27)
5'-ACGTTGGATGAGACTCAACAGGACAAGAGAC-3'

Detector Oligonucleotides:

(SEQ ID NO: 28)
5'-AAAAAAAAAAAAAAAT+G+AGGACTTGTTTTGATTGAACCAA-3'
or (SEQ ID NO: 28)
5'-AAAAAAAAAAAAAAAT+G+AGGACTTGTTTTGATTGAACCAA/
3Phos/-3'
or (SEQ ID NO: 28)
5'-AAAAAAAAAAAAAAAT+G+AGGACTTGTTTTGATTGAACCAA/
3InvdT/-3'

The following primers were used for amplification of a partial sequence within RBMY2 gene (RBMY2-1 assay):

Forward PCR primer:
(SEQ ID NO: 29)
5'-ACGTTGGATGTGCAGAAAAGACCAAAGGAATC-3'

Reverse PCR primer:
(SEQ ID NO: 30)
5'-ACGTTGGATGATAGATGCCACATAACTTGAGC-3'

Detector Oligonucleotides:

(SEQ ID NO: 31)
5'-AAAAAAAAAAAA+C+GAGGATCAGGGAGCACCC-3'
or (SEQ ID NO: 31)
5'-AAAAAAAAAAAA+C+GAGGATCAGGGAGCACCC/3Phos/-3'
or (SEQ ID NO: 31)
5'-AAAAAAAAAAAA+C+GAGGATCAGGGAGCACCC/3InvdT/-3'

The following primers were used for amplification of a partial sequence within XKRY gene (XKRY-1 assay):

Forward PCR primer:
(SEQ ID NO: 32)
5'-ACGTTGGATGAACGTTTTACCGAAGTGTTGT-3'

Reverse PCR primer:
(SEQ ID NO: 33)
5'-ACGTTGGATGAAGCCAAAGGCTAATATGTAGG-3'

Detector Oligonucleotides:

(SEQ ID NO: 34)
5'-AAAAAAAAAAAAT+G+ATGAACTACACGGCAATTATTGA-3'
or (SEQ ID NO: 34)
5'-AAAAAAAAAAAAT+G+ATGAACTACACGGCAATTATTGA/
3Phos/-3'
or -continued (SEQ ID NO: 34)
5'-AAAAAAAAAAAAT+G+ATGAACTACACGGCAATTATTGA/
3InvdT/-3'

The following primers were used for amplification of a secondary partial sequence within XKRY gene (XKRY-3 assay):

Forward PCR primer:
(SEQ ID NO: 35)
5'-ACGTTGGATGAGGCAAAATGTACTATGCCTAC-3'

Reverse PCR primer:
(SEQ ID NO: 36)
5'-ACGTTGGATGTCCTGTAGTCTCAACTATTCAG-3'

Detector Oligonucleotides:

(SEQ ID NO: 37)
5'-AAAGGAAAAA+T+GCTCACTTGGGCGAAGGAG-3'
or (SEQ ID NO: 37)
5'-AAAGGAAAAA+T+GCTCACTTGGGCGAAGGAG/3Phos/-3'
or (SEQ ID NO: 37)
5'-AAAGGAAAAA+T+GCTCACTTGGGCGAAGGAG/3InvdT/-3'

PCR Mix:

PCR primers were used at a final concentration of 900 nM for the PCR primers and at 250 nM of the detector oligonucleotide.

The PCR mix also contained 25 ng of genomic DNA (male or female), 25 ul of 2×PCR Mastermix (ABI TaqMan PCR master mix including buffer and AmpliTaq Gold enzyme) and water to a final volume of 50 ul.

Reactions were performed in a 96-well ABGene microtiter plate.

Cycling Conditions:

The PCR mix was activated for 10 minutes at 95° C. and then subjected to 55 cycles of 95° C. for 30 seconds, 60° C. for 30 s and 72° C. for 1 minute.

Sample Preparation for Mass Spectrometric Analysis:

10 ul of PCR product were transferred to a new 96-well microtiter plate and 20 ul of water containing 15 mg of ammonium-loaded ion-exchange resin (Clean Resin, SEQUENOM, Inc®) were added to the PCR product. The reaction mix was incubated for 15 minutes and gentle rotation.

A pintool device (Nanodispenser, SEQUENOM, Inc®) was used to transfer 15 nl of analyte on a miniaturized chip array (SpectroCHIP™, SEQUENOM, Inc®).

Mass Spectral Analysis:

Data acquisition and analysis was performed using a bench-top, linear MALDI-TOF mass spectrometer (Compact Analyzer, SEQUENOM, Inc®). For each spectrum at least 20 laser shots were accumulated. Presence of the target nucleic acid (here nine out of ten specific regions found on the Y chromosome) was successfully identified by the mass-distinguishable products (MDP's) of the specific detector oligonucleotides per primer set. The MALDI-TOF MS spectrum exemplifies a 90% detection rate of a 10-plex reaction. The ten MDP's are successfully generated when the target sequences (Y chromosome specific regions) are present during amplification and when the detector oligonucleotides can hybridize to the target nucleic acid during amplification.

Example 4

10-Plex Set of Y-Chromosome Markers for Gender Determination Using 5'-Biotinylated Detector Oligonucleotides and Streptavidine-Coated Magnetic Beads for Purification A detection assay was performed to detect ten regions specific for the Y-chromosome. The assay included an additional clean up step that used biotinylated detector oligonucleotides and streptavidine-coated magnetic beads for the capture of MDP's. PCR primers and detector oligonucleotides were designed to meet the criteria described in the present invention using methods well known in the art. For example, the detector oligonucleotides were designed with a melting temperature approximately 10 degrees Celsius higher than the PCR primers.

In this particular multiplexed assay, the detector oligonucleotides carry a non-complementary 5'-overhang consisting of multiple Adenines and/or Guanines. In samples where the Y-chromosome is present (such as male samples), the PCR primers and the detector oligonucleotides hybridized to the target. During amplification, the detector oligonucleotides were degraded by the 5'-nuclease activity of the DNA polymerase extending from the upstream PCR primer. During degradation, nine of the ten mass-distinguishable products (MDP's) including the 5'-polyA or polyA/G tags were released and identified unambiguously by MALDI-TOF mass spectrometric analysis. Detection of these mass signals confirmed the presence of the target nucleic acid in nine of the ten assays.

In samples where Y chromosome template is not present (such as female samples or negative control (NTC) samples) the PCR primers and the detector oligonucleotides do not hybridize to the target and 5'-polyA or polyA/G tags are not detected. Uniplex reactions carried through the entire process and then pooled to detect all assays on a single chip element also proved to be successful.

The detector oligonucleotides provided below hybridized to the target and were degraded to yield MDP's that were detected by mass spectrometry. The sequences may contain a "+", which represents a locked nucleic acid (LNA), or "/3Phos/" and "/InvdT/" which represent the introduction of a phosphate group and inverted deoxythymine, respectively. Also, the detector oligonucleotides may also contain a "Biosg/", which represents a biotin.

The following primers were used for amplification of a partial sequence within BPY2 gene (BPY2-2 assay):

Forward PCR primer:
(SEQ ID NO: 8)
5'-ACGTTGGATGATATTCTAGACTCTTCCAAGCC-3'

Reverse PCR primer:
(SEQ ID NO: 9)
5'-ACGTTGGATGAAAAAGAGGAGTGTCACTCTAC-3'

Detector oligonucleotides (multiple detector oligonucleotides were tested individually in different assays):

(SEQ ID NO: 10)
5'-5Biosg/AAAAAAAAAAAAT+T+TGCAAAGCCCAGCACTGA-3'
or

```
                                                       (SEQ ID NO: 10)
5'-5Biosg/AAAAAAAAAAAAAT+T+TGCAAAGCCCAGCACTGA/
3Phos/-3'
or (SEQ ID NO: 10)
5'-5Biosg/AAAAAAAAAAAAAT+T+TGCAAAGCCCAGCACTGA/
3InvdT-3'
```

The following primers were used for amplification of a secondary partial sequence within CDY1 gene (CDY1-1 assay):

```
    Forward PCR primer:
                                                       (SEQ ID NO: 11)
    5'-ACGTTGGATGATGTTAGCCAGGATTGTCTCG-3'

Reverse PCR primer:
                                                       (SEQ ID NO: 12)
    5'-ACGTTGGATGACACCTGTAATCCCAGCATTTT-3'
```

Detector Oligonucleotides:

```
                                                       (SEQ ID NO: 13)
5'-5Biosg/AAAAAAAAAG+C+TGAGGTGCTTGGATCACGA-3'
or
                                                       (SEQ ID NO: 13)
5'-5Biosg/AAAAAAAAAG+C+TGAGGTGCTTGGATCACGA/
3Phos/-3'
or
                                                       (SEQ ID NO: 13)
5'-5Biosg/AAAAAAAAAG+C+TGAGGTGCTTGGATCACGA/
3InvdT/-3'
```

The following primers were used for amplification of a partial sequence within CDY1 gene (CDY1-2 assay):

```
    Forward PCR primer:
                                                       (SEQ ID NO: 14)
    5'-ACGTTGGATGCAATCCCGTGTCTTTCCT-3'

Reverse PCR primer:
                                                       (SEQ ID NO: 15)
    5'-ACGTTGGATGGAACCAAATACTGTGTATTCCC-3'
```

Detector Oligonucleotides:

```
                                                       (SEQ ID NO: 16)
5'-5Biosg/AAAAAAAAA+T+GGCTTCCCAGGAGTTTGAGG-3'
or
                                                       (SEQ ID NO: 16)
5'-5Biosg/AAAAAAAAA+T+GGCTTCCCAGGAGTTTGAGG/
3Phos/-3'
or
                                                       (SEQ ID NO: 16)
5'-5Biosg/AAAAAAAAA+T+GGCTTCCCAGGAGTTTGAGG/
3InvdT/-3'
```

The following primers were used for amplification of a partial sequence within CYORF14 region of the Y chromosome (CYORF14-3 assay):

```
    Forward PCR primer:
                                                       (SEQ ID NO: 17)
    5'-ACGTTGGATGTTTACATCAACAAACAAGGG-3'
```

```
    Reverse PCR primer:
                                                       (SEQ ID NO: 18)
    5'-ACGTTGGATGCTACTGGGTCTAGCCTTATAAT-3'
```

Detector Oligonucleotides:

```
                                                       (SEQ ID NO: 19)
5'-5Biosg/AAAAGGAAAAAA+G+AGGTTGACATGAAGTCATTTGC
T-3'
or
                                                       (SEQ ID NO: 19)
5'-5Biosg/AAAAGGAAAAAA+G+AGGTTGACATGAAGTCATTTGCT/
3Phos/-3'
or
                                                       (SEQ ID NO: 19)
5'-5Biosg/AAAAGGAAAAAA+G+AGGTTGACATGAAGTCATTTGCT/
3InvdT/-3'
```

The following primers were used for amplification of a partial sequence within PRY gene (PRY-2 assay):

```
    Forward PCR primer:
                                                       (SEQ ID NO: 20)
    5'-ACGTTGGATGTCACTGGGATCAGGACAGAC-3'

Reverse PCR primer:
                                                       (SEQ ID NO: 21)
    5'-ACGTTGGATGAGAGGAAACTGCTTCCCAAAC-3'
```

Detector Oligonucleotides:

```
                                                       (SEQ ID NO: 22)
5'-5Biosg/AAAAAAAAAAAAAAA+A+GCTGCCAGCAAGGAGCCT-3'
or
                                                       (SEQ ID NO: 22)
5'-5Biosg/AAAAAAAAAAAAAAA+A+GCTGCCAGCAAGGAGCCT/
3Phos/-3'
or
                                                       (SEQ ID NO: 22)
5'-5Biosg/AAAAAAAAAAAAAAA+A+GCTGCCAGCAAGGAGCCT/
3InvdT/-3'
```

The following primers were used for amplification of a partial sequence within RBMY1A1 gene (RBMY1A1-1 assay):

```
    Forward PCR primer:
                                                       (SEQ ID NO: 23)
    5'-ACGTTGGATGGATGGGTTTTCTATGTGTGGG-3'

Reverse PCR primer:
                                                       (SEQ ID NO: 24)
    5'-ACGTTGGATGTGAGTCTCTTAATAGCACTGAG-3'
```

Detector Oligonucleotides:

```
                                                       (SEQ ID NO: 25)
5'-5Biosg/AAAAAAAAAAA+C+GGGAGGAGTCAGTGGGGA-3'
or
                                                       (SEQ ID NO: 25)
5'-5Biosg/AAAAAAAAAAA+C+GGGAGGAGTCAGTGGGGA/
3Phos/-3'
or
                                                       (SEQ ID NO: 25)
5'-5Biosg/AAAAAAAAAAA+C+GGGAGGAGTCAGTGGGGA/
3InvdT/-3'
```

The following primers were used for amplification of a secondary partial sequence within RBMY1A1 gene (RBMY1A1-2 assay):

```
Forward PCR primer:
                                    (SEQ ID NO: 26)
5'-ACGTTGGATGAGCTAATTACTCATTTCCCCAG-3'

Reverse PCR primer:
                                    (SEQ ID NO: 27)
5'-ACGTTGGATGAGACTCAACAGGACAAGAGAC-3'
```

Detector Oligonucleotides:

```
                                    (SEQ ID NO: 28)
5'-5Biosg/AAAAAAAAAAAAAAT+G+AGGACTTGTTTTGATTGAACC
AA-3'
or
                                    (SEQ ID NO: 28)
5'-5Biosg/AAAAAAAAAAAAAAT+G+AGGACTTGTTTTGATTGAACC
AA/3Phos/-3'
or
                                    (SEQ ID NO: 28)
5'-5Biosg/AAAAAAAAAAAAAAT+G+AGGACTTGTTTTGATTGAACC
AA/3InvdT/-3'
```

The following primers were used for amplification of a partial sequence within RBMY2 gene (RBMY2-1 assay):

```
Forward PCR primer:
                                    (SEQ ID NO: 29)
5'-ACGTTGGATGTGCAGAAAAGACCAAAGGAATC-3'

Reverse PCR primer:
                                    (SEQ ID NO: 30)
5'-ACGTTGGATGATAGATGCCACATAACTTGAGC-3'
```

Detector Oligonucleotides:

```
                                    (SEQ ID NO: 31)
5'-/5Biosg/AAAAAAAAAAAA+C+GAGGATCAGGGAGCACCC-3'
or
                                    (SEQ ID NO: 31)
5'-/5Biosg/AAAAAAAAAAAA+C+GAGGATCAGGGAGCACCC/
3Phos/-3'
or
                                    (SEQ ID NO: 31)
5'-/5Biosg/AAAAAAAAAAAA+C+GAGGATCAGGGAGCACCC/
3InvdT/-3'
```

The following primers were used for amplification of a partial sequence within XKRY gene (XKRY-1 assay):

```
Forward PCR primer:
                                    (SEQ ID NO: 32)
5'-ACGTTGGATGAACGTTTTACCGAAGTGTTGT-3'

Reverse PCR primer:
                                    (SEQ ID NO: 33)
5'-ACGTTGGATGAAGCCAAAGGCTAATATGTAGG-3'
```

Detector Oligonucleotides:

```
                                    (SEQ IS NO: 34)
5'-/5Biosg/AAAAAAAAAAAT+G+ATGAACTACACGGCAATTATTG
A-3'
or
                                    (SEQ ID NO: 34)
5'-/5Biosg/AAAAAAAAAAAT+G+ATGAACTACACGGCAATTATTG
A/3Phos/-3'
or
                                    (SEQ ID NO: 34)
5'-/5Biosg/AAAAAAAAAAAT+G+ATGAACTACACGGCAATTATTG
A/3InvdT/-3'
```

The following primers were used for amplification of a secondary partial sequence within XKRY gene (XKRY-3 assay):

```
Forward PCR primer:
                                    (SEQ ID NO: 35)
5'-ACGTTGGATGAGGCAAAATGTACTATGCCTAC-3'

Reverse PCR primer:
                                    (SEQ ID NO: 36)
5'-ACGTTGGATGTCCTGTAGTCTCAACTATTCAG-3'
```

```
                                    (SEQ ID NO: 37)
5'-/5Biosg/AAAGGAAAAA+T+GCTCACTTGGGCGAAGGAG-3'
or
                                    (SEQ ID NO: 37)
5'-/5Biosg/AAAGGAAAAA+T+GCTCACTTGGGCGAAGGAG/
3Phos/-3'
or
                                    (SEQ ID NO: 37)
5'-/5Biosg/AAAGGAAAAA+T+GCTCACTTGGGCGAAGGAG/
3InvdT/-3'
```

Detector Oligonucleotides:

PCR Mix:

PCR primers were used at a final concentration of 900 nM for the PCR primers and at 250 nM of the detector oligonucleotide.

The PCR mix also contained 25 ng of genomic DNA (male or female), 25 ul of 2×PCR Mastermix (ABI TaqMan PCR master mix including buffer and AmpliTaq Gold enzyme) and water to a final volume of 50 ul.

Reactions were performed in a 96-well ABGene microtiter plate.

Cycling Conditions:

The PCR mix was activated for 10 minutes at 95° C. and then subjected to 55 cycles of 95° C. for 30 seconds, 60° C. for 30 s and 72° C. for 1 minute.

Sample Preparation for Mass Spectrometric Analysis Using Streptavidine-Coated Magnetic Beads (Invitrogen Corp®):

Bead Preparation:
1. Mix and aliquot 50 ul of beads-spin and spin and remove supernatant
2. Add 75 ul of Wash Buffer (provided)-spin and remove supernatant Bead Binding:
3. Add 25 ul of Binding Buffer (provided) to beads
4. Add 35 ul of nanopure water to tube with beads
5. Add 15 ul of PCR/Nuclease reaction to tube with beads
6. Rotate 15 minutes at ambient temperature Bead Washing:
7. Spin and remove supernatant until dry
8. Wash with 1× Wash Buffer (provided)
9. Spin and remove supernatant Product Elution from Beads:
10. Add 25 μl of 25% $NH_4OH$ (freshly prepared) to beads
11. Incubate for 10 minutes at 60° C.

12. Spin and remove supernatant to a new tube (contains product)
13. Shake with lid open for 60 minutes at ambient temperature A pintool device (Nanodispenser, SEQUENOM, Inc®) was used to transfer 15 nl of analyte on a miniaturized chip array (SpectroCHIP™, SEQUENOM, Inc®).

Mass Spectral Analysis:

Data acquisition and analysis were performed using a bench-top, linear MALDI-TOF mass spectrometer (Compact Analyzer, SEQUENOM, Inc®). For each spectrum at least twenty laser shots were accumulated. Presence of the target nucleic acid (here nine out of ten specific regions found on the Y chromosome) was identified by the mass-distinguishable products (MDP's) of the specific detector oligonucleotides per primer set. The MALDI-TOF MS spectrum exemplifies a 90% detection rate of a 10-plex reaction. The nine MDP's were only generated when the target sequences (Y chromosome specific regions) were present during amplification and when the detector oligonucleotides hybridized to the target nucleic acid during amplification. Uniplex amplification followed by pooling 5 ul of each reaction yielded similar results.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, yet these modifications and improvements are within the scope and spirit of the invention.

The invention illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the invention claimed. The term "a" or "an" can refer to one of or a plurality of the elements it modifies (e.g., "a primer" can mean one or more primers) unless it is contextually clear either one of the elements or more than one of the elements is described. The term "about" as used herein refers to a value sometimes within 10% of the underlying parameter (i.e., plus or minus 10%), a value sometimes within 5% of the underlying parameter (i.e., plus or minus 5%), a value sometimes within 2.5% of the underlying parameter (i.e., plus or minus 2.5%), or a value sometimes within 1% of the underlying parameter (i.e., plus or minus 1%), and sometimes refers to the parameter with no variation. For example, a length of "about 100 nucleotides" can include lengths between 90 nucleotides and 110 nucleotides. Thus, it should be understood that although the present invention has been specifically disclosed by representative embodiments and optional features, modification and variation of the concepts herein disclosed may be resorted to by those skilled in the art, and such modifications and variations are considered within the scope of this invention.

Embodiments of the invention are set forth in the claims that follow.

What is claimed is:

1. A method of detecting the presence or absence of a target nucleic acid sequence in a sample, comprising the steps of:
   (a) contacting a sample comprising a target nucleic acid with an (i) oligonucleotide primer, comprising a 3' end and a 5' end, and comprising a sequence complementary to a region of the target nucleic acid and a (ii) detector oligonucleotide, comprising a 3' end and a 5' end, and comprising a sequence complementary to a second region of the target nucleic acid sequence which comprises a non-cleavable nucleotide incorporated at its 5' end and a contiguous nucleotide sequence that is non-complementary to the target nucleic acid sequence linked to the 5' end of the sequence complementary to the second region of the target nucleic acid sequence, thereby forming a (iii) mixture of duplexes under hybridization conditions, wherein the duplexes comprise the target nucleic acid annealed to the oligonucleotide primer and to the detector oligonucleotide such that the 3' end of the oligonucleotide primer is upstream of the 5' end of the detector oligonucleotide;
   (b) exposing the sample of step (a) to a cleavage agent under conditions sufficient to cleave and release from the annealed detector oligonucleotide, a fragment comprising the nucleotide sequence that is non-complementary to the target nucleic acid sequence thereby producing a mass-distinguishable product; and
   (c) detecting the presence or absence of the mass-distinguishable product by mass spectrometry, thereby detecting the presence or absence of the target nucleic acid sequence in the sample.

2. The method of claim 1, wherein steps a) and b) are performed simultaneously in a single, closed reaction vessel.

3. The method of claim 1, wherein two or more target nucleic acids are detected in a single, multiplexed reaction.

4. The method of claim 1, wherein more than one detector oligonucleotide is used to detect more than one target nucleic acid in a multiplexed reaction.

5. The method of claim 1, wherein the target nucleic acid comprises a mixture of nucleic acid.

6. The method of claim 5, wherein the mixture of nucleic acid comprises maternal and fetal nucleic acid, further wherein said mixture of nucleic acid has been obtained from a sample from a pregnant female.

7. The method of claim 1, wherein the cleavage agent has 5' to 3' nuclease activity.

8. The method of claim 1, wherein the non-cleavable nucleotide is a locked nucleic acids (LNA).

9. The method of claim 1, wherein the mass-distinguishable product is capable of binding to a solid support upon release.

10. The method of claim 1, wherein the mass-distinguishable product is amplified after its release.

11. The method of claim 1, wherein the detector oligonucleotide selectively binds to a methylation-specific sequence based on the methylation status of the target nucleic acid.

12. The method of claim 1, wherein the detection is done by a mass spectrometer selected from the group consisting of MALDI-TOF MS, Tandem MS, ESI-TOF, ESI-iontrap, LC-MS, GC-MS and LOI-MS.

13. The method of claim 1, wherein the detection is done in real-time.

14. The method of claim 1, wherein a competitor template nucleic acid is introduced, and further wherein the competitor template nucleic acid serves as an internal control.

15. The method of claim 1, wherein the quantity of the target nucleic acid sequence in the sample is determined.

16. The method of claim 1, wherein the detector oligonucleotide comprises a minor groove binding moiety.

17. The method of claim 7, wherein the cleavage agent is associated with a nucleic acid polymerase enzyme.

18. The method of claim 1, wherein there are more than one non-cleavable nucleotide incorporated at the 5' end of the complementary sequence.

19. The method of claim 18, wherein the more than one non-cleavable nucleotides are adjacent to each other.

* * * * *

UNITED STATES PATENT AND TRADEMARK OFFICE
CERTIFICATE OF CORRECTION

PATENT NO. : 8,133,701 B2  Page 1 of 1
APPLICATION NO. : 11/950395
DATED : March 13, 2012
INVENTOR(S) : Dirk Johannes Van Den Boom It is certified that error appears in the above-identified patent and that said Letters Patent is hereby corrected as shown below:

In column 58, line 18, please correct claim 8 to read as follows:

8. The method of claim 1, wherein the non-cleavable nucleotide is a locked nucleic acid[[s]] (LNA).

Signed and Sealed this
Twenty-sixth Day of June, 2012

David J. Kappos
*Director of the United States Patent and Trademark Office*